(12) United States Patent
Yen et al.

(10) Patent No.: US 9,793,493 B2
(45) Date of Patent: Oct. 17, 2017

(54) ORGANIC MATERIAL AND ORGANIC ELECTROLUMINESCENT DEVICE USING THE SAME

(71) Applicant: LUMINESCENCE TECHNOLOGY CORP., Hsin-Chu (TW)

(72) Inventors: Feng-Wen Yen, Taipei (TW); Cheng-Hao Chang, Miao-Li (TW)

(*) Notice: Subject to any disclaimer, the term of this patent is extended or adjusted under 35 U.S.C. 154(b) by 186 days.

(21) Appl. No.: 14/585,219

(22) Filed: Dec. 30, 2014

(65) Prior Publication Data
US 2016/0190472 A1    Jun. 30, 2016

(51) Int. Cl.
| | | |
|---|---|---|
| *H01L 51/00* | (2006.01) | |
| *C07D 401/14* | (2006.01) | |
| *C07D 401/04* | (2006.01) | |
| *C07D 251/24* | (2006.01) | |
| *C07D 209/82* | (2006.01) | |
| *C07D 403/04* | (2006.01) | |
| *C07D 403/14* | (2006.01) | |
| *C07D 405/04* | (2006.01) | |
| *C07D 333/76* | (2006.01) | |
| *C09K 11/06* | (2006.01) | |
| *H01L 51/50* | (2006.01) | |

(52) U.S. Cl.
CPC ........ *H01L 51/0072* (2013.01); *C07D 209/82* (2013.01); *C07D 251/24* (2013.01); *C07D 333/76* (2013.01); *C07D 401/04* (2013.01); *C07D 401/14* (2013.01); *C07D 403/04* (2013.01); *C07D 403/14* (2013.01); *C07D 405/04* (2013.01); *C09K 11/06* (2013.01); *H01L 51/0056* (2013.01); *H01L 51/0067* (2013.01); *H01L 51/0073* (2013.01); *H01L 51/0074* (2013.01); *C09K 2211/1011* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *H01L 51/5016* (2013.01); *H01L 51/5072* (2013.01); *H01L 51/5096* (2013.01); *H01L 2251/5384* (2013.01)

(58) Field of Classification Search
None
See application file for complete search history.

(56) References Cited

U.S. PATENT DOCUMENTS

| | | |
|---|---|---|
| 2014/0131664 A1 | 5/2014 | Yen et al. |
| 2014/0151645 A1 | 6/2014 | Yen et al. |
| 2014/0166988 A1 | 6/2014 | Yen et al. |
| 2014/0175384 A1 | 6/2014 | Yen et al. |
| 2014/0209866 A1 | 7/2014 | Yen |
| 2014/0231754 A1 | 8/2014 | Yen |

FOREIGN PATENT DOCUMENTS

| | | | | |
|---|---|---|---|---|
| JP | 2013232520 A | 11/2013 | | |
| KR | 10-2013-0007934 A | * 1/2013 | ............ | C09K 11/06 |
| WO | WO-2013-009079 A1 | * 1/2013 | ............ | C09K 11/06 |

OTHER PUBLICATIONS

Machine English translation of Bae et al. (KR 10-2013-0007934 A). Sep. 8, 2016.*

* cited by examiner

*Primary Examiner* — J. L. Yang

(57) ABSTRACT

The present invention discloses an novel organic material is represented by the following formula (A) and organic EL device using the organic material as hole blocking layer (HBL), electron transport layer (ETL) or phosphorescent host can efficiently lower driving voltage, lower power consumption and increase the efficiency.

formula(A)

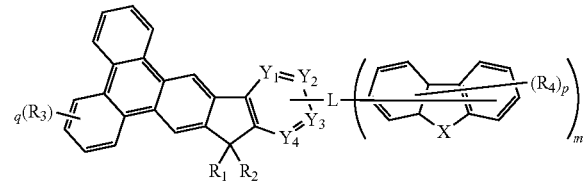

The same definition as described in the present invention.

10 Claims, 1 Drawing Sheet

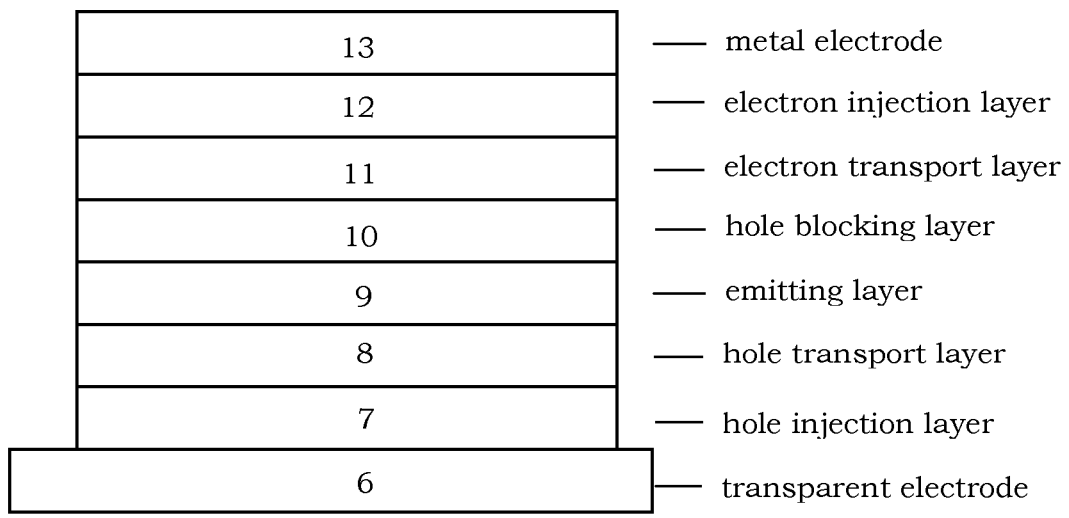

ORGANIC MATERIAL AND ORGANIC ELECTROLUMINESCENT DEVICE USING THE SAME

FIELD OF INVENTION

The present invention generally relates to an organic material and organic electroluminescent (herein referred to as organic EL) device using the organic material. More specifically, the present invention relates to an organic material having general formula (A), an organic EL device employing the organic material as hole blocking layer (HBL), electron transport layer (ETL) or phosphorescent host can efficiently lower driving voltage, lower power consumption and increase the efficiency.

BACKGROUND OF THE INVENTION

Organic electroluminescent (organic EL) is a light-emitting diode (LED) in which the emissive layer is a film made by organic compounds which emits light in response to an electric current. The emissive layer of organic compound is sandwiched between two electrodes. Organic EL is applied in flat panel displays due to their high illumination, low weight, ultra-thin profile, self-illumination without back light, low power consumption, wide viewing angle, high contrast, simple fabrication methods and rapid response time.

The first observation of electroluminescence in organic materials were in the early 1950s by Andre Bernanose and co-workers at the Nancy-University in France. Martin Pope and his co-workers at New York University first observed direct current (DC) electroluminescence on a single pure crystal of anthracene and on anthracene crystals doped with tetracene under vacuum in 1963.

The first diode device was reported by Ching W. Tang and Steven Van Slyke at Eastman Kodak in 1987. The device used a two-layer structure with separate hole transporting and electron transporting layers resulted in reduction in operating voltage and improvement of the efficiency, that led to the current era of organic EL research and device production.

Typically organic EL is composed of layers of organic materials situated between two electrodes, which include a hole transporting layer (HTL), an emitting layer (EML), an electron transporting layer (ETL). The basic mechanism of organic electroluminescence involves the injection of the carrier, transport, recombination of carriers and exciton formed to emit light. When an external voltage is applied to an organic light-emitting device, electrons and holes are injected from a cathode and an anode, respectively, electrons will be injected from a cathode into a LUMO (lowest unoccupied molecular orbital) and holes will be injected from an anode into a HOMO (highest occupied molecular orbital). When the electrons recombine with holes in the emitting layer, excitons are formed and then emit light. When luminescent molecules absorb energy to achieve an excited state, an exciton may either be in a singlet state or a triplet state depending on how the spins of the electron and hole have been combined. 75% of the excitons form by recombination of electrons and holes to achieve a triplet excited state. Decay from triplet states is spin forbidden, Thus, a fluorescence electroluminescent device has only 25% internal quantum efficiency. In contrast to fluorescence electroluminescent device, phosphorescent organic light-emitting diodes make use of spin-orbit interactions to facilitate intersystem crossing between singlet and triplet states, thus obtaining emission from both singlet and triplet states and the internal quantum efficiency of electroluminescent devices from 25% to 100%.

Recently, a new type of fluorescent organic EL device incorporating mechanism of thermally activated delayed fluorescence (TADF) has been developed by Adachi and coworkers is a promising way to obtain a high efficiency of exciton formation by converting spin-forbidden triplet excitons up to the siglet level by the mechanism of reverse intersystem crossing (RISC).

The phosphorescent organic EL utilizes both triplet and singlet excitons. Cause of longer lifetime and the diffusion length of triplet excitons compared to those of singlet excitons, the phosphorescent organic EL generally need an additional hole blocking layer (HBL) between the emitting layer (EML) and the electron transporting layer (ETL) or the electron transporting layer with hole blocking ability instead of typical ETL. The purpose of the use of HBL or HBETL is to confine the recombination of injected holes and electrons and the relaxation of created excitons within the EML, hence the device's efficiency can be improved. To meet such roles, the hole blocking materials must have HOMO (highest occupied molecular orbital) and LUMO (lowest unoccupied molecular orbital) energy levels suitable to block hole transport from the EML to the ETL and to pass electrons from the ETL to the EML, in addition, lower power consumption, the good thermal and electrochemical stability of the materials are also needed.

There continues to be a need for organic EL materials which is able to efficiently transport electrons and block holes, with lower power consumption, good thermal stability and high emitting efficiency. According to the reasons described above, the present invention has the objective of resolving such problems of the prior-art and offering an organic EL device which is excellent in its lower power consumption, thermal stability, high luminance and long half-life time. The present invention disclose a novel organic material having general formula (A), used as hole blocking layer (HBL), electron transport layer (ETL) or phosphorescent host have good charge carrier mobility and excellent operational durability can efficiently lower driving voltage and power consumption, increasing efficiency of organic EL device.

SUMMARY OF THE INVENTION

In accordance with the present invention, the organic material for hole blocking material (herein referred to as HBM), electron transport material (herein referred to as ETM) or phosphorescent host and their use for organic EL device are provided. The organic can overcome the drawbacks of the conventional materials like as lower efficiency and higher power consumption.

An object of the present invention is to provide the organic material which can be used as hole blocking material (HBM), hole blocking electron transport material (HBETM) for organic EL device and can efficiently confine excitons to transfer to electron transport layer.

An object of the present invention is to provide the organic material which can be used as electron transport material (ETM) for organic EL device.

An object of the present invention is to provide the organic material which can be used as phosphorescent host material of emitting layer for organic EL device.

Another object of the present invention is to apply the organic material for organic EL device and lower driving voltage, lower power consumption and increase the efficiency.

The present invention has the economic advantages for industrial practice. Accordingly the present invention, the organic material which can be used for organic EL device is disclosed. The mentioned the organic material is represented by the following formula (A):

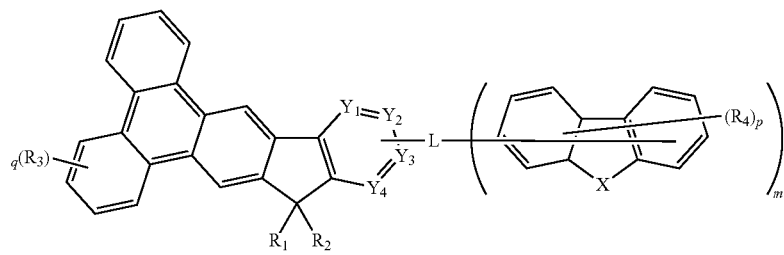

formula (A)

Wherein m represent 0 to 2, and when m represent 1 or 2, L represent a single bond, a substituted or unsubstituted arylene group having 6 to 40 ring carbon atoms, or a substituted or unsubstituted heterarylene group having 3 to 40 ring carbon atoms. When m represent 0, L represent a substituted or unsubstituted heterarylene group having 3 to 40 ring carbon atoms. X represent O, S, $NR_5$. $Y_1$ to $Y_4$ each independently represent nitrogen atom or $CR_6$. $R_5$ and $R_6$ independently represent a hydrogen atom, a substituent, or a bond to L. p represent an integer of 0 to 7, q represent an integer of 0 to 10. $R_1$ to $R_4$ independently selected from the group consisting of a hydrogen atom, a halide, alkyl group having 1 to 20 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 3 to 30 carbon atoms.

According to the formula (A), when L are not represented single bond, m represent 1 or 2, some preferable arylene group and heterarylene group for L are consisting of group represent as:

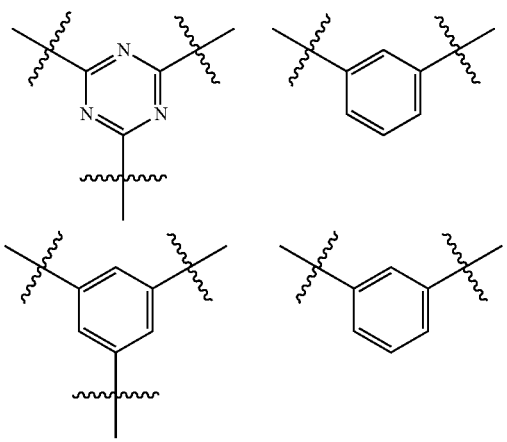

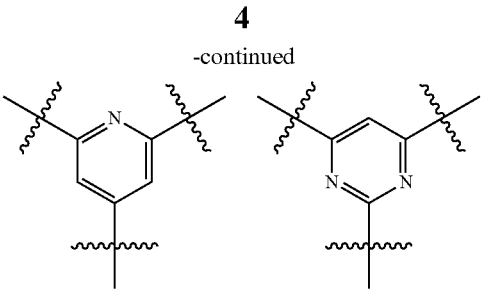

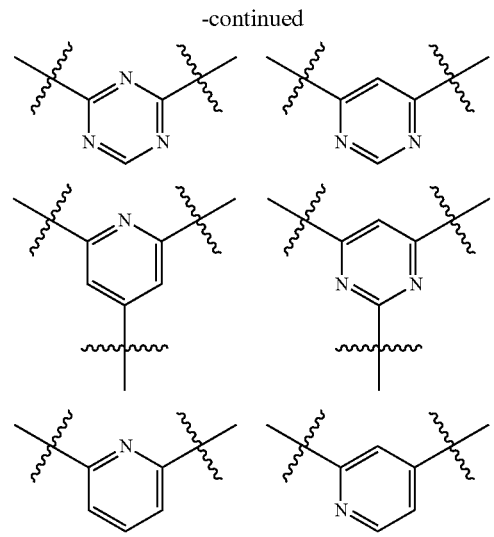

According to the formula (A), when L are not represented single bond, m represent 0, some preferable heterarylene group for L are consisting of group represent as

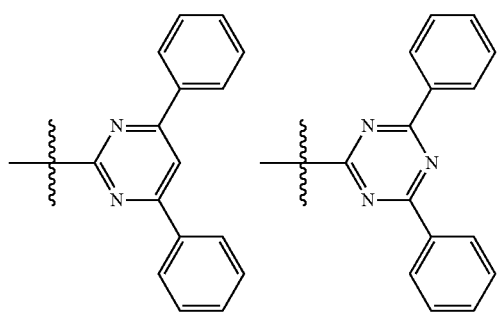

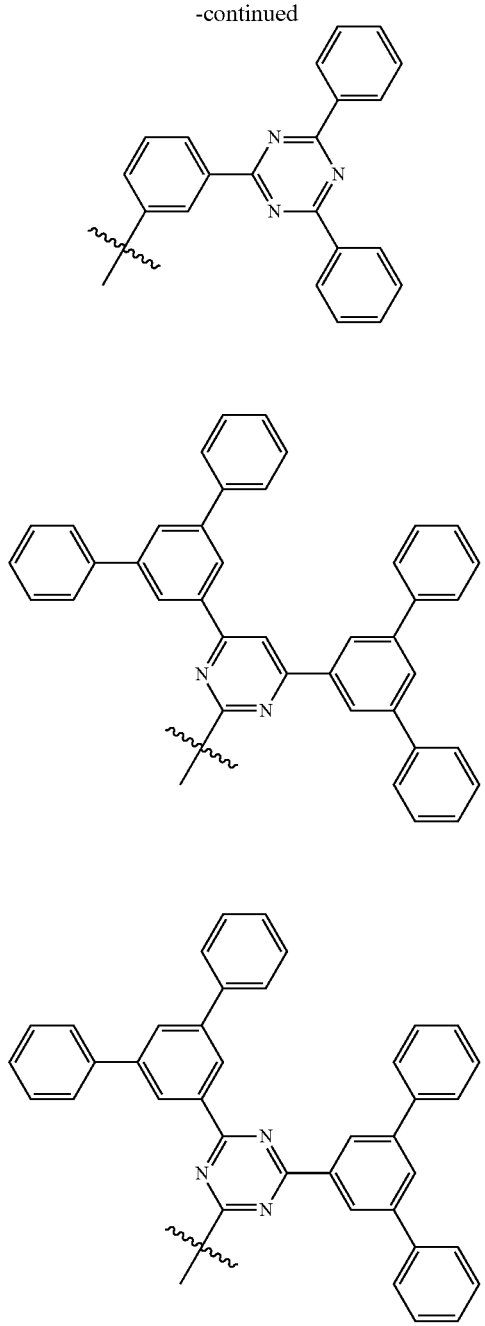

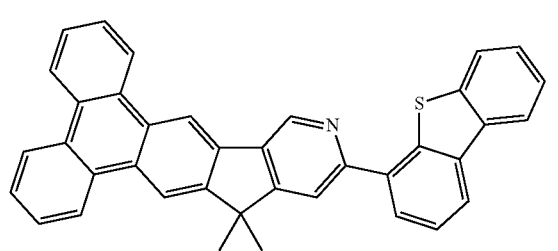

BRIEF DESCRIPTION OF THE DRAWINGS

The FIGURE show one example of organic EL device in the present invention. 6 is transparent electrode, 13 is metal electrode, 7 is hole injection layer which is deposited onto 6, 8 is hole transporting layer which is deposited onto 7, 9 is fluorescent or phosphorescent emitting layer which is deposited onto 8, 10 is hole blocking layer or hole blocking electron transporting layer which is deposited onto 9, 11 is electron transporting layer which is deposited onto 10, 12 is electron injection layer which is deposited on to 11.

In this embodiment, some organic materials according formula (A) are shown below:

-continued
A6
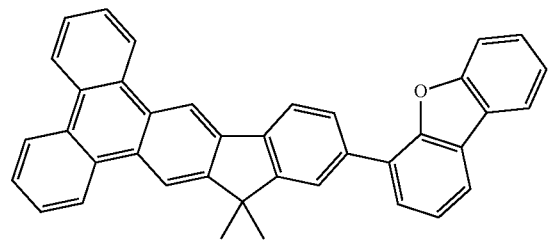
A7
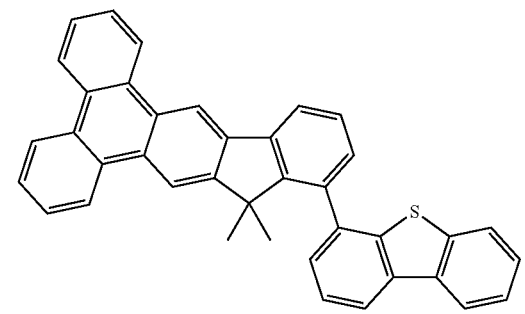
A8
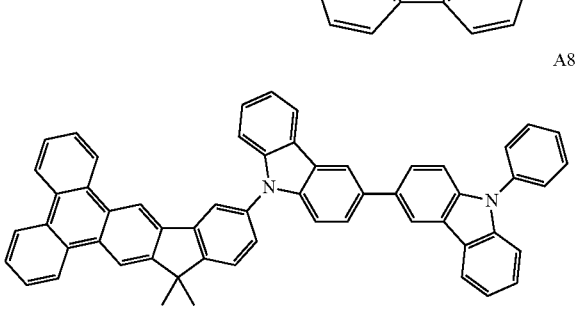
A9
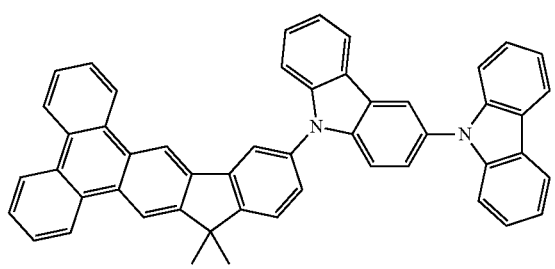
A10
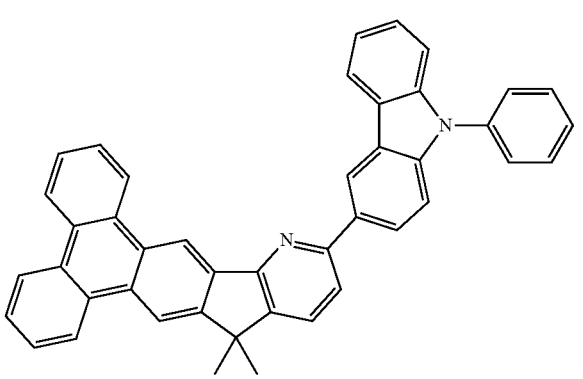
-continued
A11
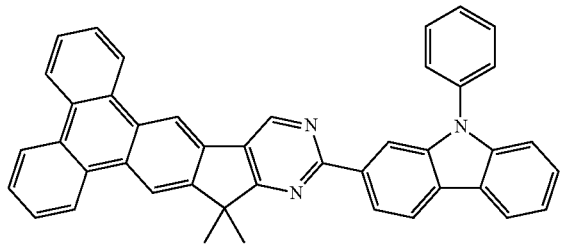
A12
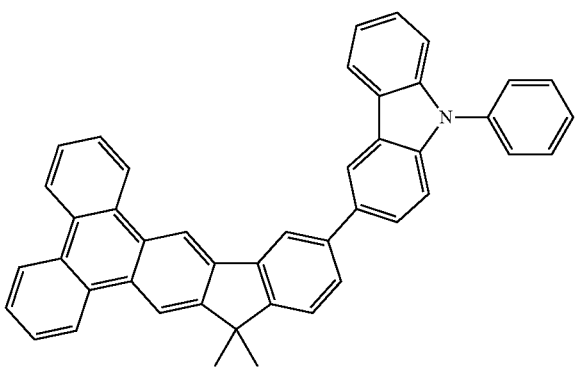
A13
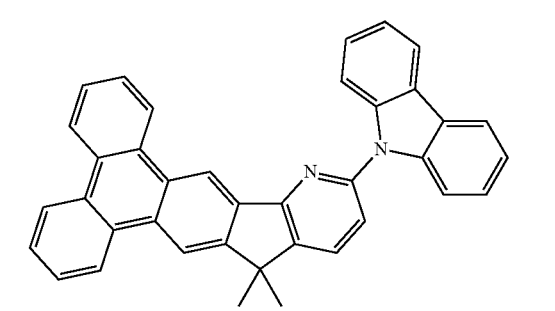
A14
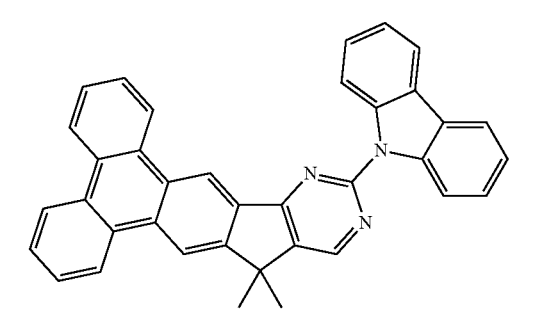
A15
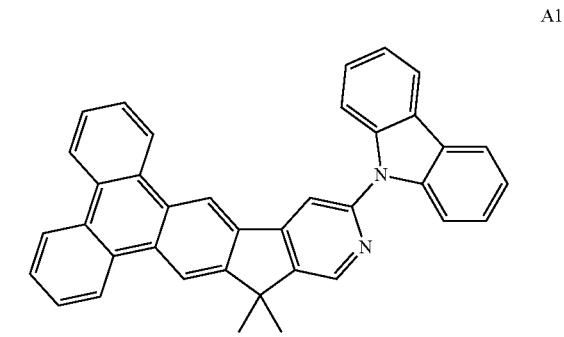

A16
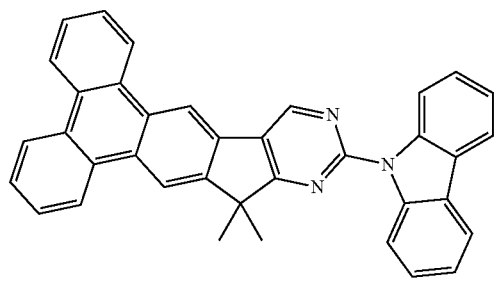
A17
A18
A19
A20
A21
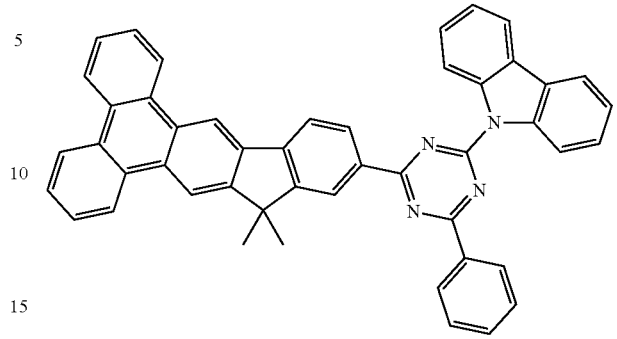
A22
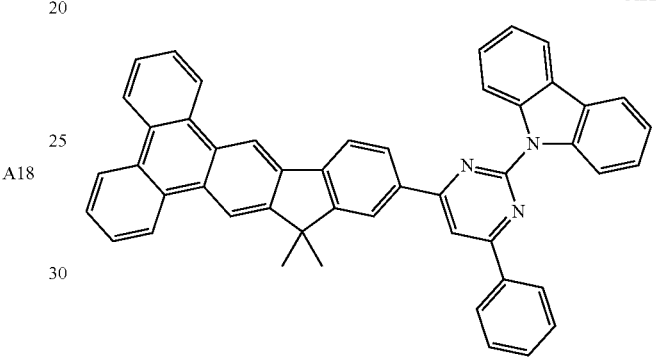
A23
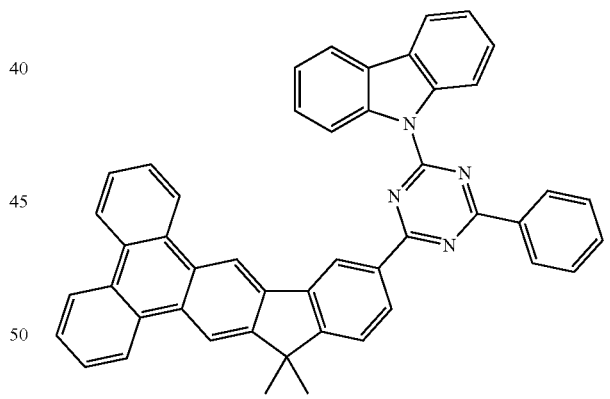
A24
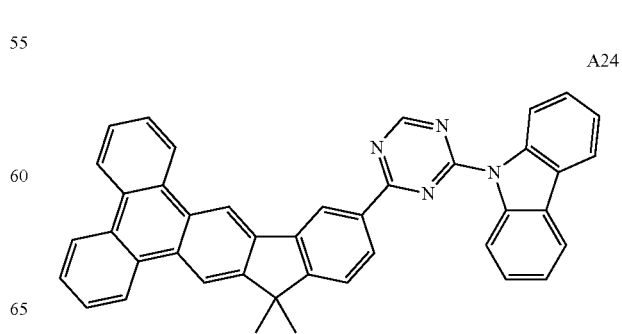

A25
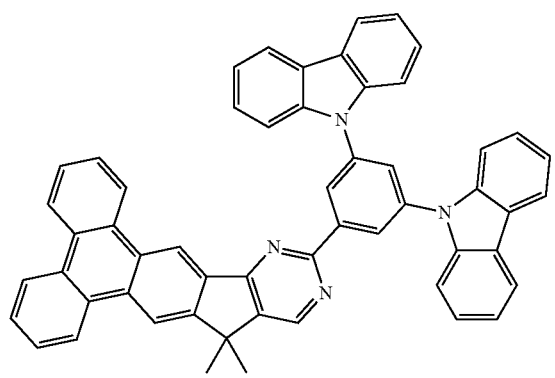
A26
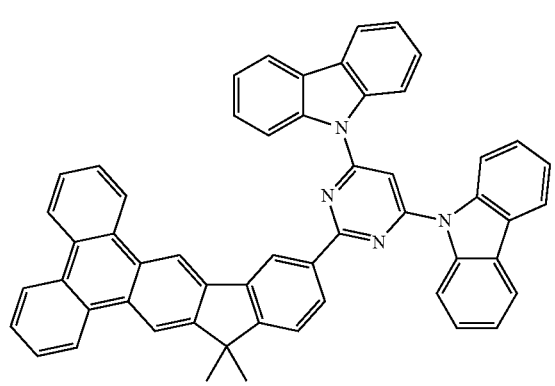
A27
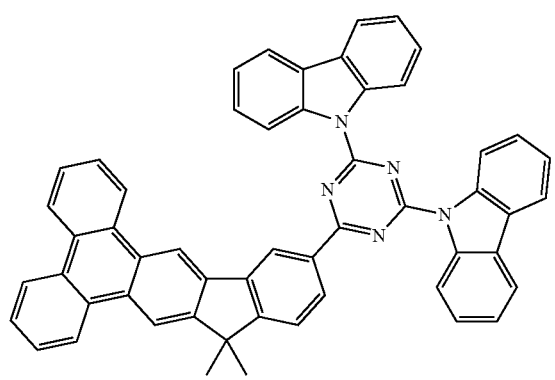
A28
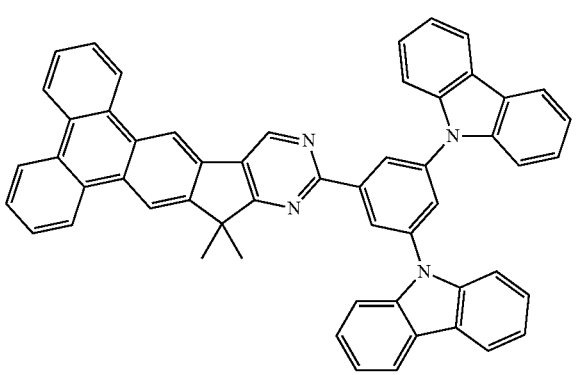
A29
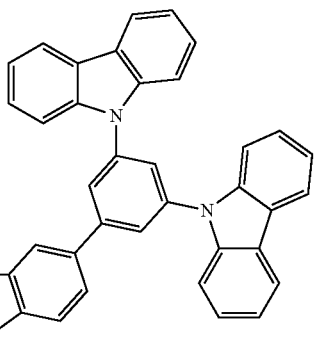
A30
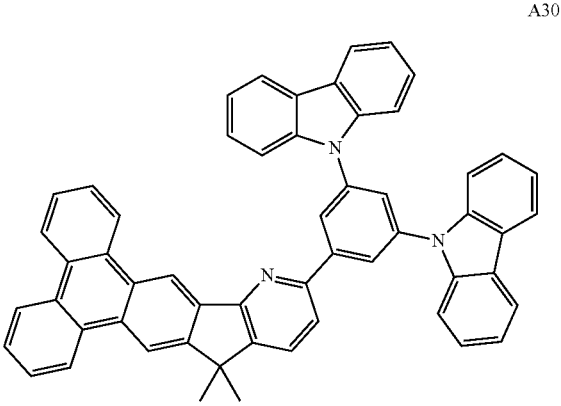
A31
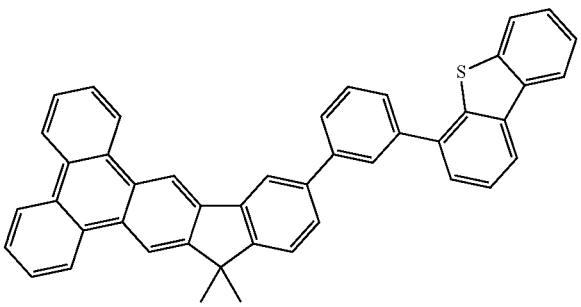
A32
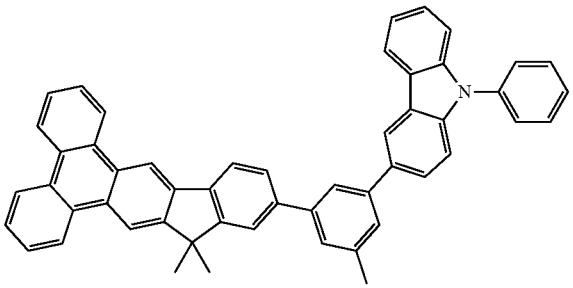

A33
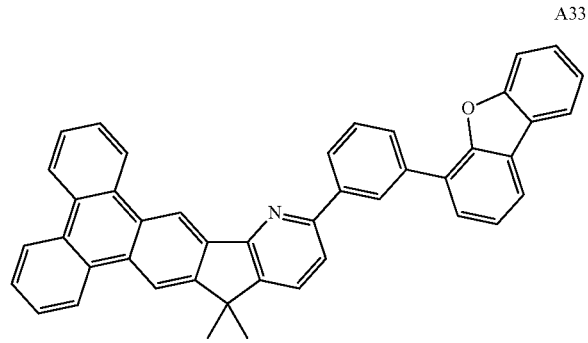
A34
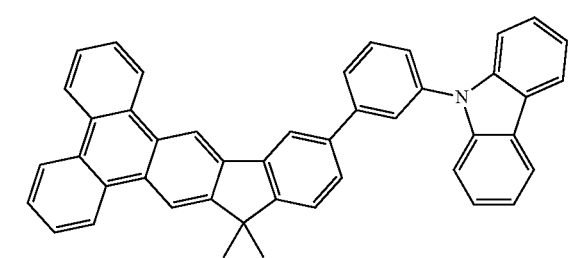
A35
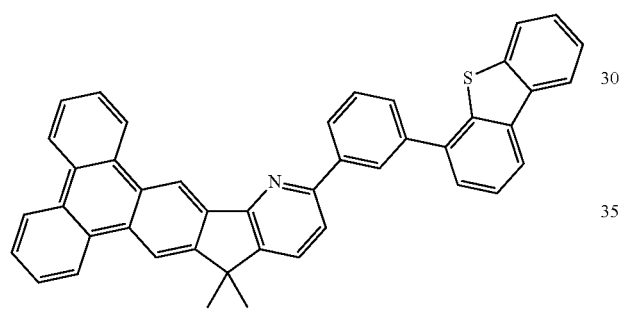
A36
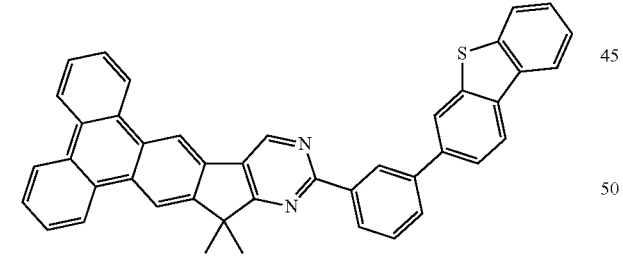
A37
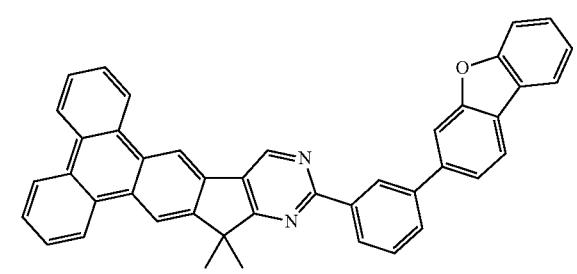
A38
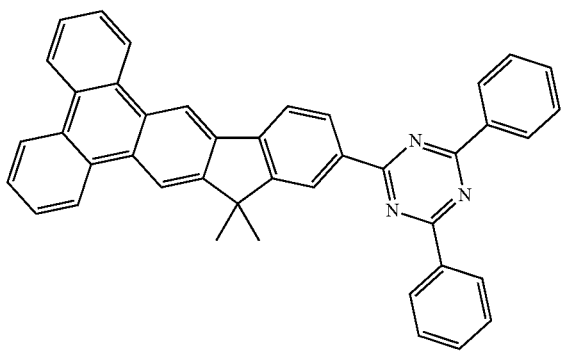
A39
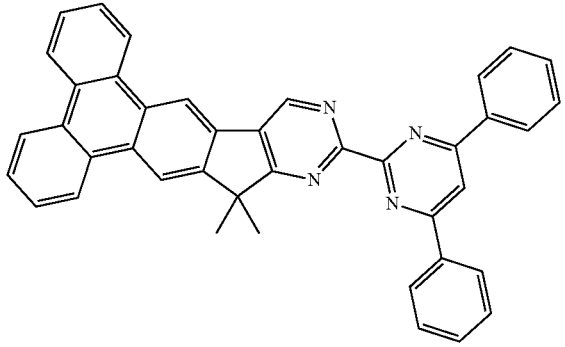
A40
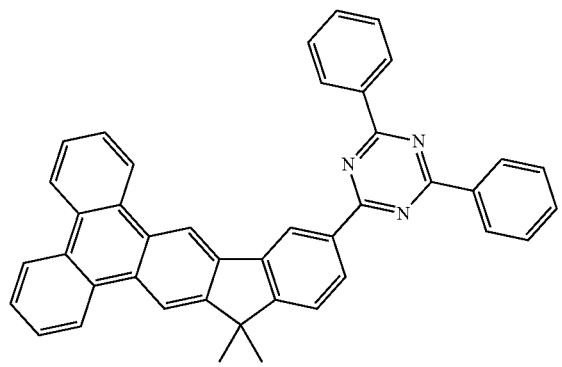
A41
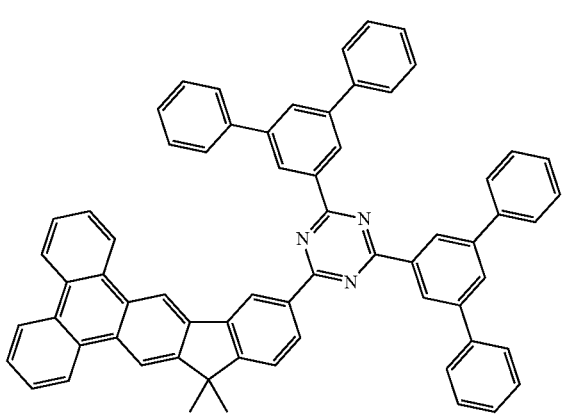

-continued

A42

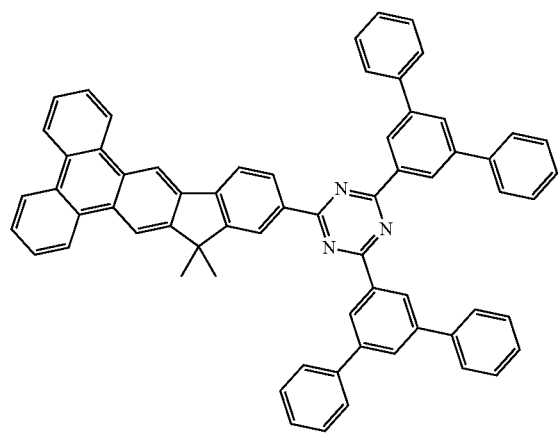

Detailed preparation for the organic material in the present invention could be clarified by exemplary embodiments, but the present invention is not limited to exemplary embodiments. Intermediate Ia~Ig and EXAMPLE 1~17 show the preparation for some EXAMPLES of the organic material in the present invention. EXAMPLE 18 and 19 show the fabrication of organic EL device and I-V-B, half-life time of organic EL device testing report.

Synthesis of Intermediate Ia

Synthesis of methyl 2-phenylnicotinate

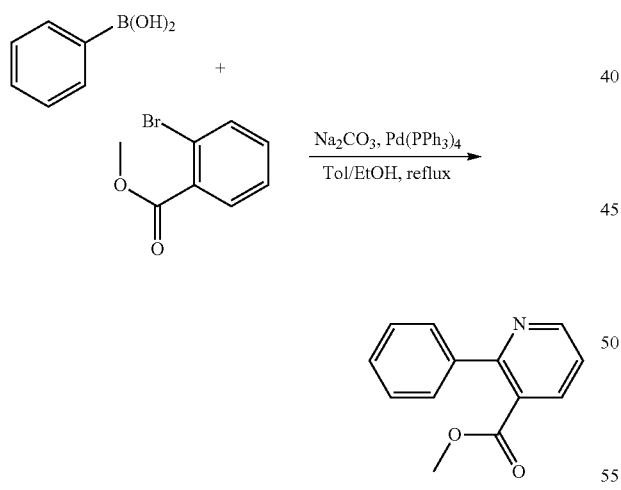

A mixture of methyl 2-bromonicotinate (10.8 g, 50 mmol), phenylboronic acid (6.1 g, 50 mmol), 2M Na$_2$CO$_3$ (100 ml, 200 mmol), and Pd(PPh$_3$)$_4$ (1.5 g, 1 mmol) was dissolved in 300 ml toluene/100 ml ethanol under N$_2$. After stirring for 24 h at 80° C., the mixture was allowed to cool to room temperature. The residue was extract using dichloromethane/water, and organic layer was evaporated to dryness. The residue was purified by column chromatography on silica gel to obtained 6.1 g of methyl 2-phenylnicotinate. Yield 57.2%.

Synthesis of 5,5-dimethyl-5H-indeno[1,2-b]pyridine

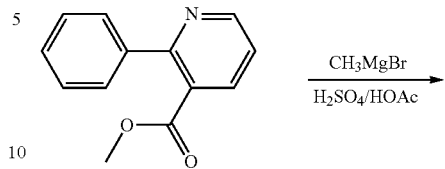

The methyl 2-phenylnicotinate (10.6 g, 50 mmol) is dissolved in THF (20 ml), followed by adding 35 ml of CH$_3$MgBr (3M in ether). The refluxing reaction is held for overnight then stopped. After extraction with ethyl acetate, drying with anhydrous magnesium sulfate, rotary evaporation to remove solvent, intermediate product is obtained. The intermediate product is then dissolved in mixed solution of acetic acid (100 ml) and sulfuric acid (5 ml). The refluxing reaction is held for 4 hours then stopped and cooled. After extraction with ethyl acetate, drying with anhydrous magnesium sulfate, rotary evaporation to remove solvent, the residue was purified by column chromatography on silica gel to obtain 3.1 g of 5,5-dimethyl-5H-indeno[1,2-b]pyridine (31.8% yield)

Synthesis of 7-bromo-5,5-dimethyl-5H-indeno[1,2-b]pyridine

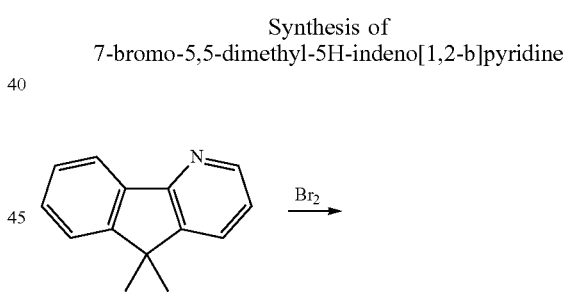

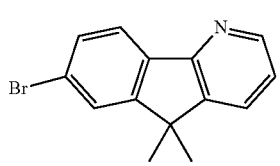

5,5-dimethyl-5H-indeno[1,2-b]pyridine (3.9 g, 20 mmol) was dissolved in chloroform (300 ml), protected from light and bromine (3.2 g, 20 mmol) diluted in chloroform (10 ml) was added drop wise. The mixture was stirred for 24 hours at room temperature, after which water (600 ml) was added, then the precipitated product was filtered off with suction, washed with MeOH and recrystallized from chloroform to give the 7-bromo-5,5-dimethyl-5H-indeno[1,2-b]pyridine 3.7 g. Yield 67.5%

Synthesis of 7-(biphenyl-2-yl)-5,5-dimethyl-5H-indeno[1,2-b]pyridine

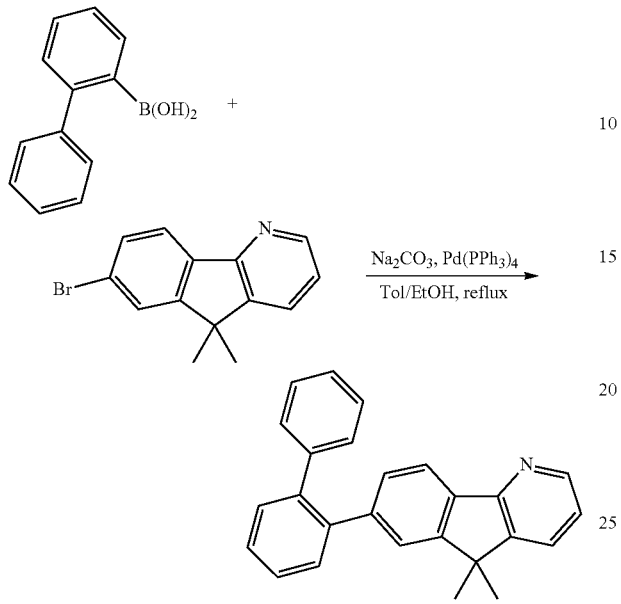

A mixture of 7-bromo-5,5-dimethyl-5H-indeno[1,2-b]-pyridine (10 g, 36.5 mmol), biphenyl-2-ylboronic acid (7.2 g, 36.5 mmol), Pd(PPh$_3$)$_4$ (0.43 g, 0.368 mmol), 2M Na$_2$CO$_3$ (37 ml), 50 ml of EtOH and 150 ml toluene was degassed and placed under nitrogen, and then heated at 90° C. for 24 h. After finishing the reaction, the reaction mixture was cool to room temperature. The organic layer was extracted with ethyl acetate and water, dried with anhydrous magnesium sulfate, the solvent was removed and the residue was purified by column chromatography on silica gel to obtain 7-(biphenyl-2-yl)-5,5-dimethyl-5H-indeno[1,2-b]pyridine 8.4 g. Yield 66%.

Synthesis of Intermediate Ia

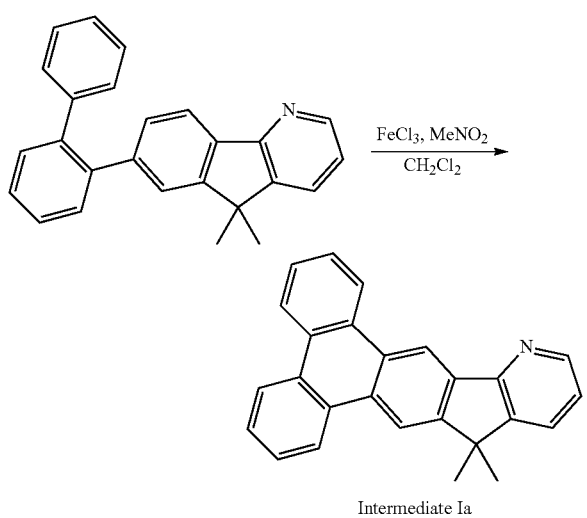

Under nitrogen condition, 7-(biphenyl-2-yl)-5,5-dimethyl-5H-indeno[1,2-b]-pyridine (3.47 g, 10 mmol) was dissolved in anhydrous dichloromethane (250 ml), 1.62 g (100 mmol) Iron(III) chloride was then added, and the mixture was stirred one hour. Methanol 10 ml were added to the mixture and the organic layer was separated and the solvent removed in vacuum. The residue was purified by column chromatography on silica gel to obtain 1.4 g of the product. Yield 40%.

Synthesis of Intermediate Ib

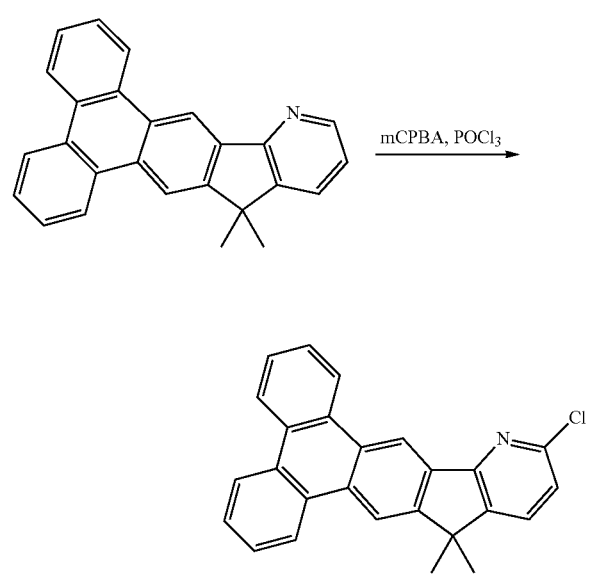

13.82 g (40 mmol) of intermediate Ia was dissolved in 100 ml of chloroform, 9.2 g (52 mmol) of mCPBA was added to the solution at 25° C., with stirring, and stirred at room temperature for 2 hours. After the reaction, sodium thiosulfate was added to the mixture, and dried over sodium sulfate and filtrated. The filtrate was concentrated and the slurry was washed with chloroform, the crude material was purified by chromatography on silica gel to obtain 5.8 g of an N-oxide of Intermediate Ia. Yield 41%.

Subsequently, 15 ml of phosphorus oxychloride was added to 5.8 g (16 mmol) of the above N-oxide, and heated and stirred at 95° C. for 10 hours. The reaction was concentrated, and then chloroform (200 ml) was added to the concentrate. The chloroform solution was added dropwise to a saturated aqueous solution of sodium hydrogen carbonate, and stirred for 1 hour. The mixture was extracted with chloroform, washed with sat. NaCl$_{(aq)}$, dried over sodium sulfate, and concentrated, the crude material was purified by chromatography on silica gel to give 3.1 g. Yield 51%.
$^1$HNMR (CDCl$_3$, 400 MHz): chemical shift (ppm) 8.75 (s, 1H), 8.49~8.44 (m, 3H), 8.32~8.28 (m, 3H), 8.14~8.06 (m, 4H), 7.77 (d, J=8.0 Hz, 1H), 1.63 (s, 6H).

EXAMPLE 1

Synthesis of Compound A1

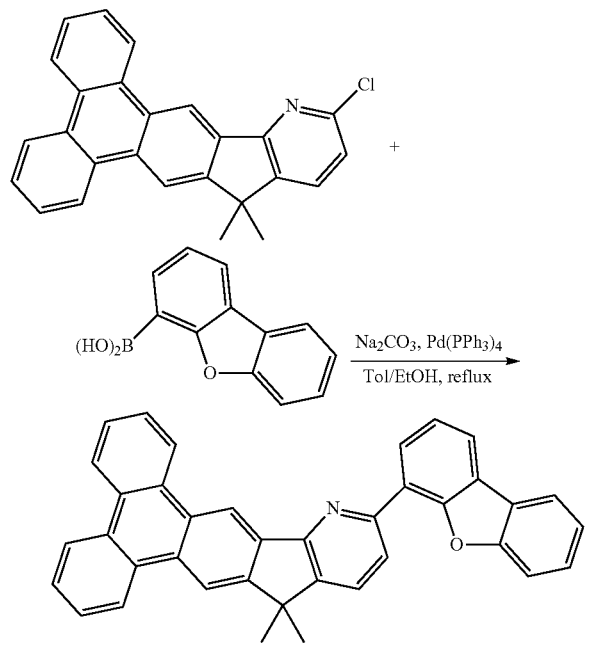

A three-necked 250 ml flask was charged with Intermediate Ib (10 mmol), dibenzo[b,d]furan-4-ylboronic acid (10 mmol), Pd(PPh$_3$)$_4$ (0.25 g, 0.21 mmol), aqueous Na$_2$CO$_3$ (2M, 12 ml, 24 mmol), ethanol (15 ml), and toluene (50 ml). The mixture was degassed and refluxed for 24 h under nitrogen atmosphere. After being cooled, water (50 ml) was added to the mixture. The crude product was collected as a solid powder by filtration and washed with methanol several times to remove impurity. It was dried at 60° C. under vacuum and gave a product in 52.1% yield. MS (m/z, FAB+): 511.2. $^1$H NMR (CDCl$_3$, 400 MHz): chemical shift (ppm) 9.44 (s, 1H), 8.90 (m, 2H), 8.12~8.08 (m, 4H), 7.92~7.81 (m, 6H), 7.42~7.31 (m, 5H), 7.10 (d, J=8.0 Hz, 1H), 1.76 (s, 6H).

EXAMPLE 2

Synthesis of Compound A30

Synthesis of 9,9'-(5-(4,4,5,5-tetramethyl-1,3,2-dioxaborolan-2-yl)-1,3-phenylene)bis(9H-carbazole)

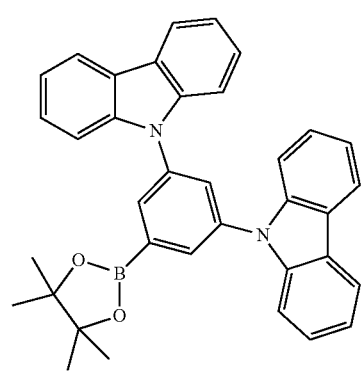 [SMILES: CC1(C)OB(c2cc(-n3c4ccccc4c4ccccc43)cc(-n3c4ccccc4c4ccccc43)c2)OC1(C)C]

1,3-dibromo chlorobenzene (8.11 g, 39 mmol), carbazole (13.7 g, 82 mmol), palladium acetate (450 mg, 2 mmol), t-butyl phosphine (6 ml, 1M solution), sodium t-butoxide (15 g, 156 mmol) and dry o-xylene (250 ml) were placed in a four-necked flask. The mixture was reacted at 125° C. for 30 hours under nitrogen. After cooling to room temperature, the reaction solution was poured into water, extracted with chloroform and washed with sat. NaCl$_{(aq)}$. Then, dried over anhydrous magnesium sulfate and the solvent were removed with an evaporator. The residue was purified by column chromatography and 4 g of 3,5-di(carbazol-9-yl)chlorobenzene was obtained. Yield 23.2%.

In a four-necked flask, 3,5-di(carbazol-9-yl)chlorobenzene (4 g, 9 mmol), bis(pinacolato)diboron (2.4 g, 9.4 mmol), KOAc (2.5 g, 25.8 mmol), Pd$_2$(dba)$_3$ (258 mg, 0.284 mmol), tricyclohexylphosphine (385 mg, 1.4 mmol) and anhydrous 1,4-dioxane (120 ml) were placed. The mixture was reacted for overnight at 80° C. under nitrogen for 16 hours. The reaction solution was poured into water, extracted with ethyl acetate and washed with sat. NaCl$_{(aq)}$. Then, dried over anhydrous magnesium sulfate and the solvent was removed with an evaporator. The residue was purified by column chromatography and 1.5 g of product was obtained. Yield 32%.

Synthesis of Compound A30

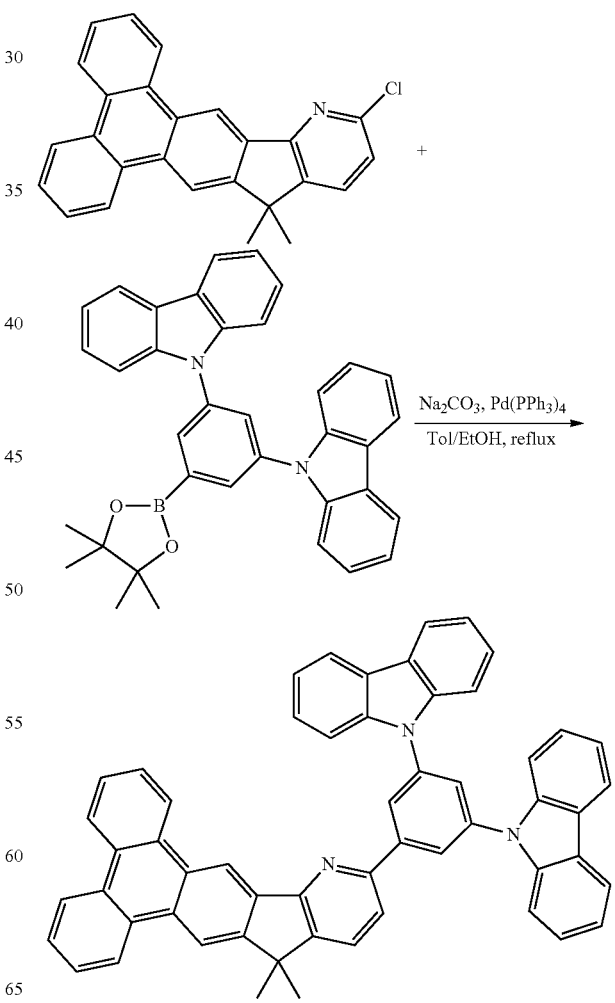

The synthesis of procedures are the same process with compound A1, the yield of the final product is 56.8%. MS (m/z, FAB+): 751.4 ¹H NMR (CDCl₃, 400 MHz): chemical shift (ppm) 9.54 (s, 1H), 8.92 (d, J=8.0 Hz, 1H), 8.72~8.64 (m, 4H), 8.19~8.13 (m, 4H), 8.05 (s, 1H), 7.96~7.86 (m, 6H), 7.62~7.56 (m, 5H), 7.35~7.28 (m, 7H), 7.02 (s, 1H), 1.66 (s, 6H).

EXAMPLE 3

Synthesis of Compound A33

Synthesis of 2-(3-(dibenzo[b,d]furan-4-yl)phenyl)-4,4,5,5-tetramethyl-1,3,2-dioxaborolane

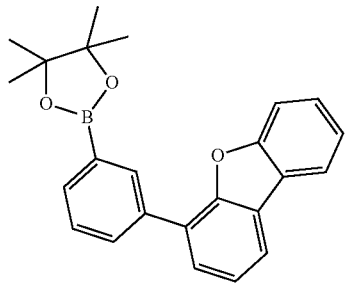 [SMILES: CC1(C)OB(c2cccc(-c3cccc4c3oc3ccccc34)c2)OC1(C)C]

A mixture of 4-dibenzofuranboronic acid (10 g, 47 mmol), 1-Bromo-3-iodo-benzene (14.7 g, 52 mmol), and Pd(PPh₃)₄ (0.55 g) in 250 mL of toluene and 150 ml of ethanol was heated and degas for 30 minutes, then 2M Na₂CO₃₍aq₎ (94 ml) was added. The reaction mixture refluxed for overnight at 100° C. The mixture was then cooled to room temperature and diluted with 300 ml ethyl acetate. The organic layer was washed with 2×300 mL portions of water, 2×300 ml portions of sat. NaCl₍ac₎, and dried with anhydrous magnesium sulfate. After the solution was concentrated, the residue was purified by column chromatography to afford 4-(3-Bromo-phenyl)-dibenzofuran 8.5 g. Yield 56%.

5.76 g of 4-(3-Bromo-phenyl)-dibenzofuran (17.8 mmol), 5.43 g of bis(pinacolato)diboron (21.4 mmol), and 0.582 g of Pd (dppf)Cl₂ (4% mol) were dissolved with heating in 100 ml 1,4-dioxane and then treated with KOAc (5.25 g, 53.5 mmol). The reaction mixture was stirred at reflux for 16 hr, cooled to room temperature and diluted with ethyl acetate. The organic layer was washed with sat. NaCl₍aq₎, dried over anhydrous magnesium sulfate, filtered and concentrated in vacuum. The residue was purified by flash column chromatography with to yield the product 4.81 g. Yield 73%.

Synthesis of Compound A33

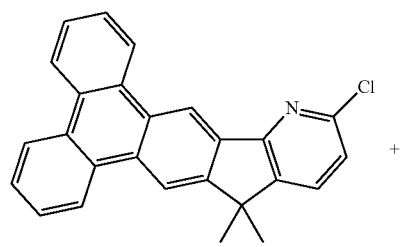

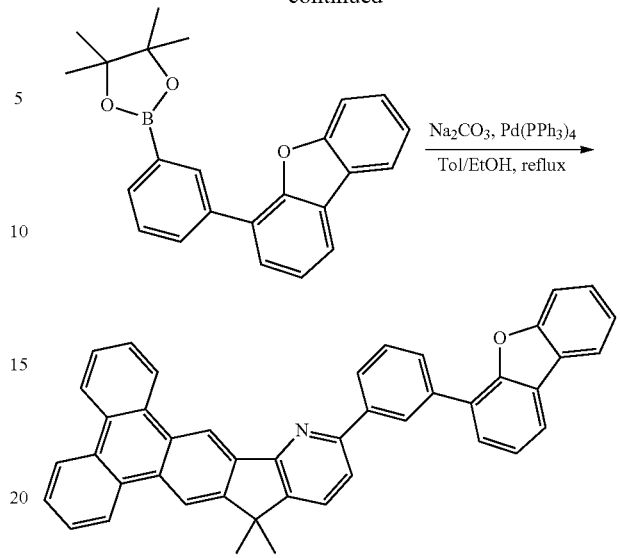

The synthesis of procedures are the same process with compound A1, the yield of the final product is 52.1%. MS (m/z, FAB+): 587.1 ¹H NMR (CDCl₃, 400 MHz): chemical shift (ppm) 9.47 (s, 1H), 8.91 (m, 2H), 8.17~8.13 (m, 2H), 8.07~8.01 (m, 3H), 7.93~7.81 (m, 8H), 7.62~7.51 (m, 3H), 7.22~7.17 (m, 3H), 7.04 (d, J=8.0 Hz, 1H), 1.70 (s, 6H).

EXAMPLE 4

Synthesis of Compound A13

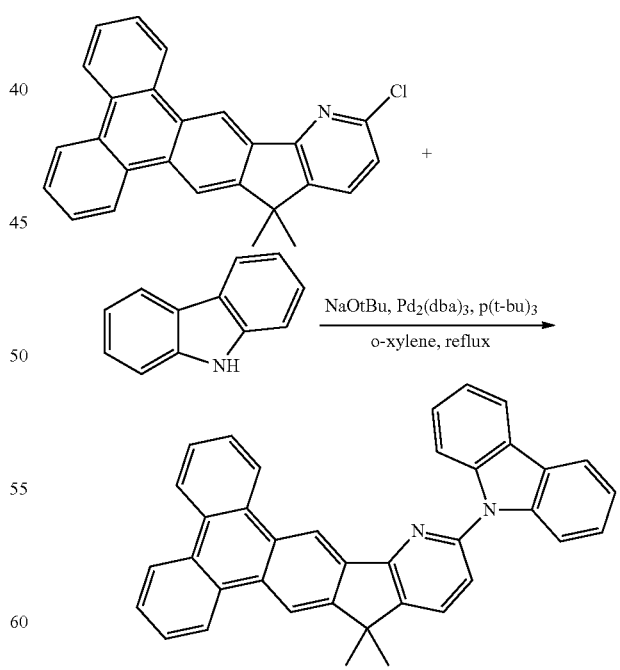

Carbazole (3.34 g, 20 mmol), intermediate Ib (3.80 g, 10 mmol), 18-Crown-6 (0.32 g, 1.96 mmol), potassium carbonate (2.5 g, 1.8 mmol), Pd₂(dba)₃ (0.1 g, 0.12 mmol) and tri-tert-butylphosphine (0.5 ml, 0.5 mmol, 1.0 M in toluene)

were mixed in 50 ml of o-xylene. The mixture was stirred under N₂ for 30 minutes, and the mixture was heated to reflux under N₂ for overnight. The o-xylene solution was decanted. The solvent was then evaporated and residue was purified by column chromatography. 2.65 g of product was obtained. Yield 52%. MS (m/z, FAB+): 510.3 ¹HNMR (CDCl₃, 400 MHz): chemical shift (ppm) 9.04 (s, 1H), 8.80~8.76 (m, 2H), 8.73~8.66 (m, 5H), 7.76~7.63 (m, 5H), 7.38~7.31 (m, 4H), 7.42~7.28 (m, 2H), 7.20 (d, J=8 Hz, 1H), 1.67 (s, 6H).

Synthesis of intermediate Ic

Synthesis of 2-(biphenyl-2-yl)-6-bromo-9,9-dimethyl-9H-fluorene

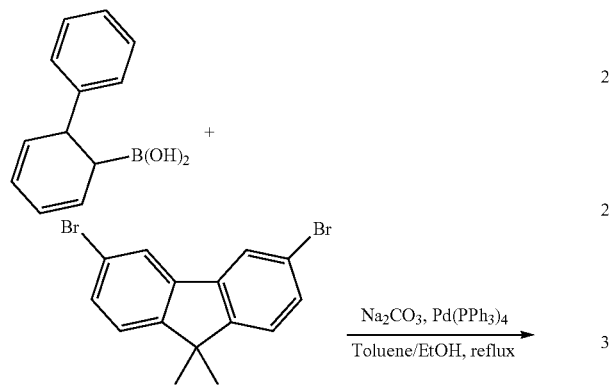

A mixture of 35.2 g (100 mmol) of 3,6-dibromo-9,9-dimethyl-9H-fluorene, 21.8 g (110 mmol) of biphenyl-2-ylboronic acid, 2.31 g (2 mmol) of Pd(PPh₃)₄, 75 ml of 2M Na₂CO₃, 150 ml of EtOH and 300 ml toluene was degassed and placed under nitrogen, and then heated at 100° C. for 12 h. After finishing the reaction, the mixture was allowed to cool to room temperature. The organic layer was extracted with ethyl acetate and water, dried with anhydrous magnesium sulfate, the solvent was removed and the residue was purified by column chromatography on silica to give product (26.8 g, 63.0 mmol, 63%) as a white solid.

Synthesis of Intermediate Ic

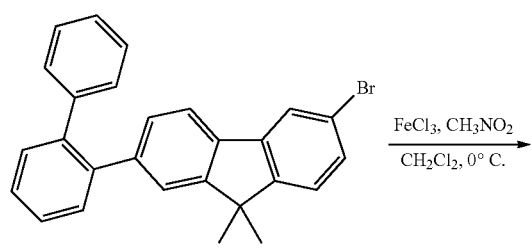

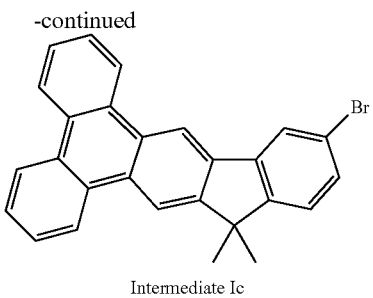

Intermediate Ic

In a 3000 ml three-necked flask that had been degassed and filled with nitrogen, 26.8 g (60 mmol) of 2-(biphenyl-2-yl)-7-bromo-9,9-dimethyl-9H-fluorene was dissolved in anhydrous dichloromethane (1500 ml), 97.5 g (600 mmol) Iron(III) chloride was then added, and the mixture was stirred one hour. Methanol 500 ml were added to the mixture and the organic layer was separated and the solvent removed in vacuo. The residue was purified by column chromatography on silica (hexane-dichloromethane) afforded a white solid (10.7 g, 25.3 mmol, 40%). ¹H NMR (CDCl₃, 500 MHz): chemical shift (ppm) 8.93 (s, 1H), 8.77~8.71 (m, 2H), 8.67~8.65 (m, 3H), 8.08 (d, J=1.5 Hz, 1H), 7.71~7.64 (m, 4H), 7.49 (dd, J₁=8.5 Hz, J₂=1.5 Hz, 1H), 7.37 (d, J=8.5 Hz, 1H), 1.62 (s, 6H).

Synthesis of Intermediate Id

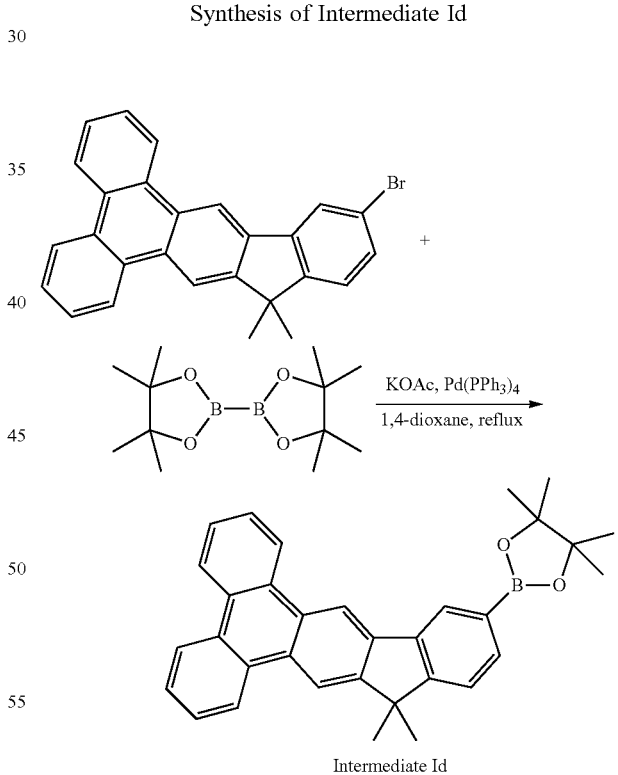

Intermediate Id

A mixture of 10.7 g (25.3 mmol) of intermediates Ic, 7.7 g (30.3 mmol) of bis(pinacolato)diboron, 0.3 g (0.26 mmol) of Pd(PPh₃)₄, 7.4 g (75.4 mmol) of potassium acetate, and 500 ml 1,4-dioxane was degassed and placed under nitrogen, and then heated at 90° C. for 16 h. After finishing the reaction, The mixture was allowed to cool to room temperature. The organic phase separated and washed with ethyl acetate and water. After drying over magnesium sulfate, the solvent was removed in vacuum. The residue was purified by column chromatography on silica to give product (9.5 g, 20.2 mmol, 80%) as a light-yellow solid; $^1$H NMR (CDCl$_3$, 500 MHz): chemical shift (ppm) 8.93 (s, 1H), 8.77~8.71 (m, 2H), 8.67~8.65 (m, 3H), 7.88 (d, J=1.5 Hz, 1H), 7.71~7.64 (m, 4H), 7.29 (dd, J$_1$=8.5 Hz, J$_2$=1.5 Hz, 1H), 7.42 (d, J=8.5 Hz, 1H), 1.62 (s, 6H), 1.42 (s, 12H).

EXAMPLE 5

Synthesis of Compound A2

EXAMPLE 6

Synthesis of Compound A12

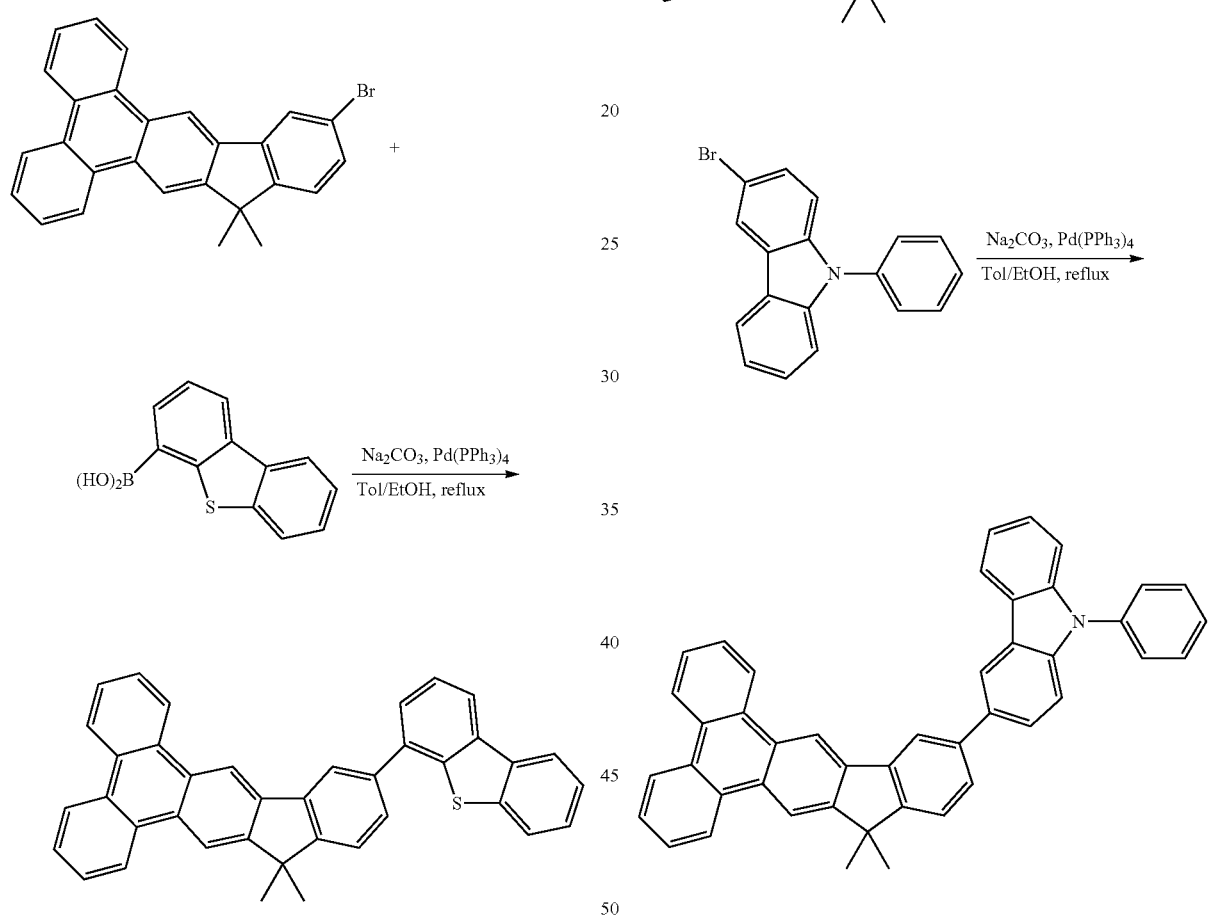

A three-necked 250 ml flask was charged with intermediate Ic 4.2 g (10 mmol), dibenzo[b,d]thiophen-4-ylboronic acid 2.3 g (10 mmol), Pd(PPh$_3$)$_4$ (0.25 g, 0.21 mmol), aqueous Na$_2$CO$_3$ (2M, 12 ml, 24 mmol), ethanol (15 ml), and toluene (50 ml). The mixture was degassed and refluxed for 24 h under nitrogen atmosphere. After being cooled, water (50 ml) was added to the mixture. The crude product was collected as a solid powder by filtration and washed with methanol several times to remove impurity. The residue was purified by column chromatography on silica (hexane-dichloromethane) afforded a white solid (2.1 g, 40%). MS (m/z, FAB+): 526.2 $^1$H NMR (CDCl$_3$, 400 MHz): chemical shift (ppm) 8.94 (s, 1H), 8.80 (m, 2H), 8.62~8.51 (m, 4H), 7.92~7.84 (m, 6H), 7.55~7.45 (m, 5H), 7.29 (d, J=8.0 Hz, 1H), 1.69 (s, 6H).

A mixture of 4.4 g (10 mmol) of intermediate Id, 3.2 g (10 mmol) of 3-bromo-9-phenyl-9H-carbazole, 0.23 g (0.2 mmol) of tetrakis(triphenyl phosphine)palladium, 15 ml of 2M Na$_2$CO$_3$, 20 ml of EtOH and 40 ml toluene was degassed and placed under nitrogen, and then heated at 90° C. overnight. After finishing the reaction, the mixture was allowed to cool to room temperature. Than 100 ml of MeOH was added, while stirring and the precipitated product was filtered off with suction. To give 3.7 g (yield 63%) of yellow product which was recrystallized from toluene. MS (m/z, FAB+): 585.3 $^1$H NMR (CDCl$_3$, 400 MHz): chemical shift (ppm) 8.96 (s, 1H), 8.81 (d, J=8 Hz, 1H), 8.76 (d, J=8 Hz, 1H), 8.67~8.60 (m, 4H), 7.73~7.66 (m, 6H), 7.53~7.43 (m, 10H), 7.21~7.16 (m, 2H), 1.66 (s, 6H).

EXAMPLE 7

Synthesis of Compound A20

Synthesis of 9-(4-(3-bromophenyl)-6-phenylpyrimidin-2-yl)-9H-carbazole

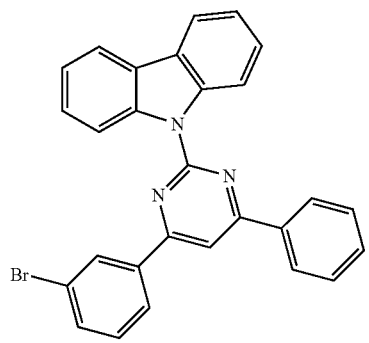 [SMILES: Brc1cccc(-c2cc(-c3ccccc3)nc(-n3c4ccccc4c4ccccc43)n2)c1]

A mixture of 4,6-diiodo-2-chloropyrimidine (18.3 g, 50 mmol), phenylboronic acid (6.1 g, 50 mmol), K$_2$CO$_3$ (13.8 g, 100 mmol), and Pd(PPh$_3$)$_4$ (1.16 g, 1 mmol) was dissolved in 500 ml 1,4-dioxane/20 ml H$_2$O under N$_2$. After stirring for 24 h at 80° C., the mixture was allowed to cool to room temperature. The solid was removed by filtration, and the filtrate was evaporated to dryness. The residue was purified by column chromatography on silica gel to obtained 8.3 g of 2-chloro-4-iodo-6-phenylpyrimidine. Yield 52.3%

A mixture of 2-chloro-4-iodo-6-phenylpyrimidine (8.3 g, 26.2 mmol), 3-bromo-phenylboronic acid (3.2 g, 26.2 mmol), K$_2$CO$_3$ (7.2 g, 52.4 mmol), and Pd(PPh$_3$)$_4$ (0.58 g, 0.5 mmol) was dissolved in 200 ml 1,4-dioxane/10 ml H$_2$O under N2. After stirring for 24 h at 80° C., the mixture was allowed to cool to room temperature. The solid was removed by filtration, and the filtrate was evaporated to dryness. The residue was purified by column chromatography on silica gel to obtained 4.1 g of 4-(3-bromophenyl)-2-chloro-6-phenyl-pyrimidine. Yield 45.2%

A mixture of 4-(3-bromophenyl)-2-chloro-6-phenyl-pyrimidine (4.1 g, 11.9 mmol), carbazole (2.2 g, 13 mmol), tri-tert-butylphosphonium tetra fluoroborate (0.7 g, 2.4 mmole) and Pd$_2$(dba)$_3$ (0.55 g, 5 mol %) were dissolved in 300 ml of o-xylene and 2.9 g of sodium-tert-butoxide, under N$_2$. The resulting solution was heated to reflux for overnight. After cooled to room temperature, the residue was extract for 3 times using CH$_2$Cl$_2$/water. The organic layer was collected and evaporated. The resulting crude product was purified by chromatography to obtained 2.6 g of product. Yield 45.9%.

Synthesis of Compound A20

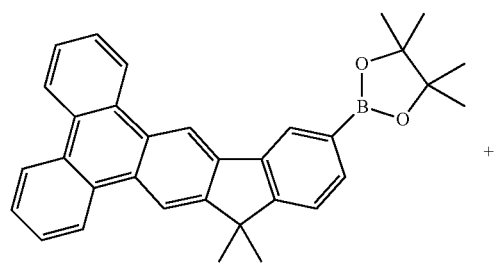

+

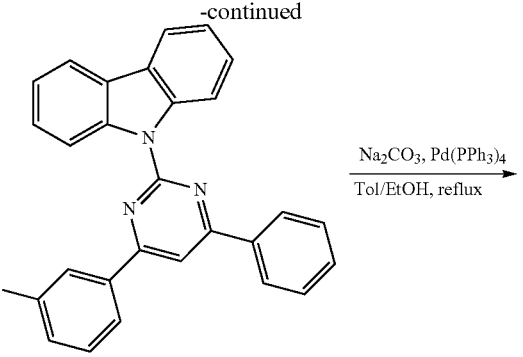

$\xrightarrow{\text{Na}_2\text{CO}_3,\ \text{Pd(PPh}_3)_4}{\text{Tol/EtOH, reflux}}$ -continued

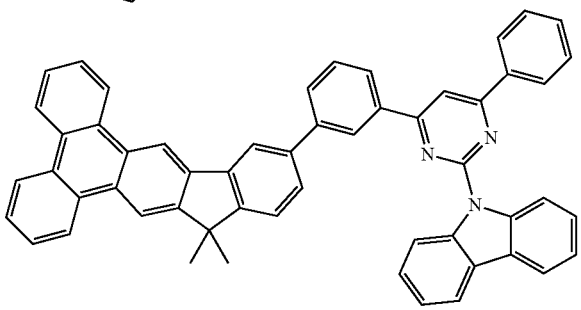

The synthesis of procedures are the same process with compound A12, the yield of the final product is 48.4%. MS (m/z, FAB+): 739.3 $^1$H NMR (CDCl$_3$, 400 MHz): chemical shift (ppm) 9.14 (s, 1H), 8.86 (d, J=8 Hz, 1H), 8.80 (d, J=8 Hz, 1H), 8.73 (s, 1H), 8.63~8.48 (m, 6H), 7.84~7.67 (m, 13H), 7.42~7.28 (m, 8H), 1.66 (s, 6H).

EXAMPLE 8

Synthesis of Compound A23

Synthesis of 9-(4-chloro-6-phenyl-1,3,5-triazin-2-yl)-9H-carbazole

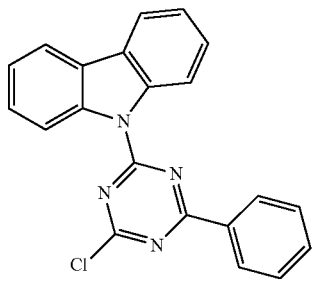 [SMILES: Clc1nc(-c2ccccc2)nc(-n2c3ccccc3c3ccccc32)n1]

10 g (54 mmol) of cyanuric chloride was added 50 ml of dry THF, then 54 ml of phenylmagnesium bromide (1.0 mol in THF) was added dropwise at 0° C., and the mixture was stirred at 0° C. for 3 hours. The reaction solution were added 50 ml of water and 100 ml of toluene, the organic layer was dried over anhydrous magnesium sulfate, and the solvent was distilled off under reduced pressure. The solid thus washed with hexane and 6 g of 2,4-dichloro-6-phenyl-1,3,5-triazine was obtained. Yield 49.2%.

Under a N$_2$ condition, 80 ml of THF was added to 3.9 g (102 mmol) of sodium hydride (62.2% dispersion in oil) and stirred at room temperature for 30 minutes. To the suspension thus obtained was added a solution of 16.5 g (96 mmol) of carbazole in DMF (100 ml), the reaction mixture was stirred at room temperature for 1 hour. The resulting suspension was added 20.3 g (90 mmol) of 2,4-dichloro-6-phenyl-1,3,5-triazine and stirred at 60° C. for 40 minutes. The reaction mixture was cooled to room temperature, 300 ml of water was added with stirring, and the precipitated solid was collected by filtration. The solid was purified by silica gel column chromatography to obtained 14 g of product. Yield 43.6%.

Synthesis of Compound A23

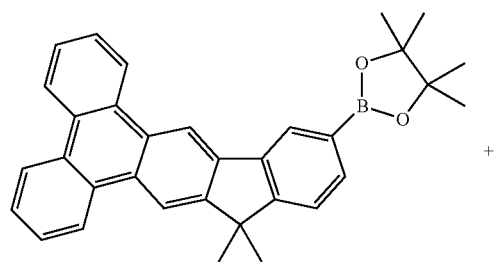

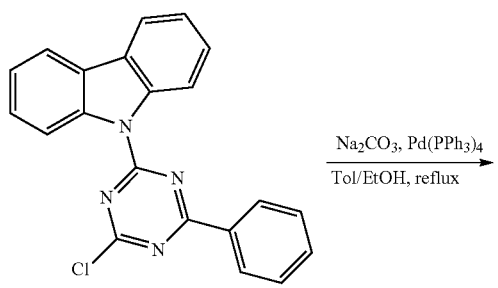

The synthesis of procedures are the same process with compound A12, the yield of the final product is 48.4%. MS (m/z, FAB+): 664.3. $^1$HNMR (CDCl$_3$, 400 MHz): chemical shift (ppm) 8.96 (s, 1H), 8.83 (d, J=8 Hz, 1H), 8.74 (d, J=8 Hz, 1H), 8.75~8.57 (m, 10H), 7.78~7.59 (m, 4H), 7.44~7.23 (m, 7H), 7.16~7.14 (m, 2H), 1.66 (s, 6H).

EXAMPLE 9

Synthesis of Compound A27

Synthesis of 9,9'-(6-chloro-1,3,5-triazine-2,4-diyl) bis(9H-carbazole)

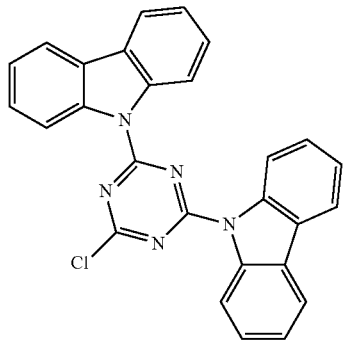 [SMILES: Clc1nc(-n2c3ccccc3c3ccccc32)nc(-n2c3ccccc3c3ccccc32)n1]

Under N$_2$, carbazole (28.4 g, 170 mmol) was dissolved in 800 ml of dry THF in a 4-neck round-bottom flask. n-Buthyllithium (1.6M in hexane solution) (100 ml, 160 mmol) was added dropwise to the carbazole solution and the mixture was stirred for 15 minutes. In another three-necked, round-bottom flask, cyanuric chloride (14.8 g, 80 mmol) was dissolved in 400 ml of dry THF in an N$_2$ atmosphere. The carbazole lithium solution was added dropwise to the cyanuric chloride solution using a transfer canula within 30 minutes. The reaction mixture was refluxed for 6 h. After the solution was cooled to room temperature, 500 ml of water was added. The product was filtered off, washed with water, hexane, and diethyl ether and further purified by hot filtration from ethanol. 20 g of product was obtained. Yield 56.1%.

Synthesis of Compound A27

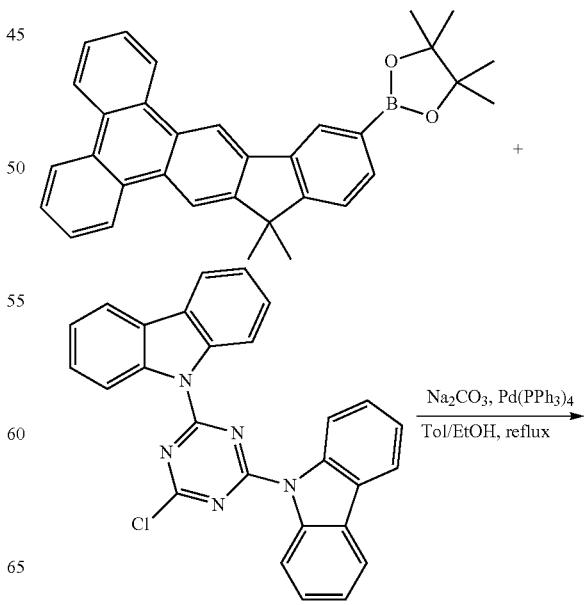

-continued

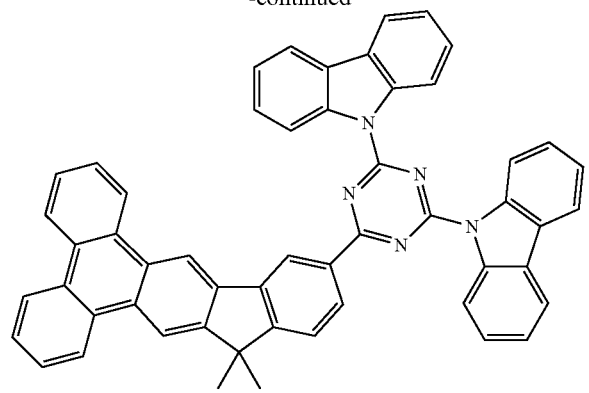

The synthesis of procedures are the same process with compound A12, the yield of the final product is 52.2%. MS (m/z, FAB+): 753.4. $^1$HNMR (CDCl$_3$, 400 MHz): chemical shift (ppm) 9.04 (s, 1H), 8.84 (d, J=8 Hz, 1H), 8.82 (d, J=8 Hz, 1H), 8.69~8.58 (m, 8H), 8.07~8.02 (m, 6H), 7.76~7.67 (m, 6H), 7.40~7.36 (m, 3H), 7.14~7.08 (m, 3H), 1.62 (s, 6H).

EXAMPLE 10

Synthesis of Compound A31

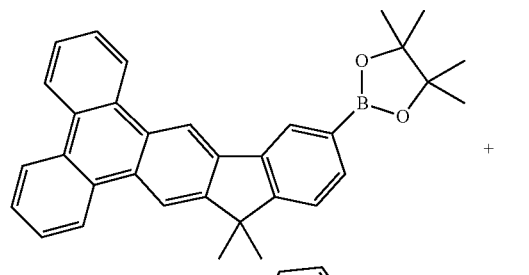

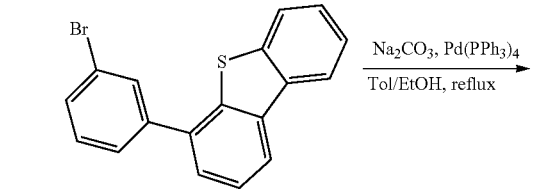

28

The synthesis of procedures are the same process with compound A12, the yield of the final product is 41%. MS (m/z, FAB+): 602.4. $^1$H NMR (CDCl$_3$, 400 MHz): chemical shift (ppm) 8.94 (s, 1H), 8.80 (d, J=8 Hz, 1H), 8.74 (d, J=8 Hz, 1H), 8.72~8.64 (m, 7H), 8.52~8.49 (m, 2H), 7.78~7.59 (m, 6H), 7.42~7.28 (m, 5H), 7.16 (d, J=8 Hz, 1H), 1.67 (s, 6H).

EXAMPLE 11

Synthesis of Compound A34

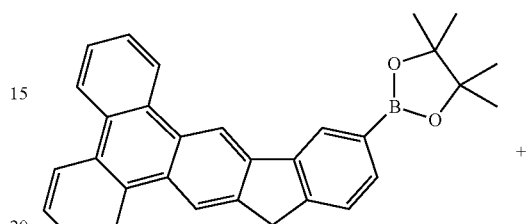

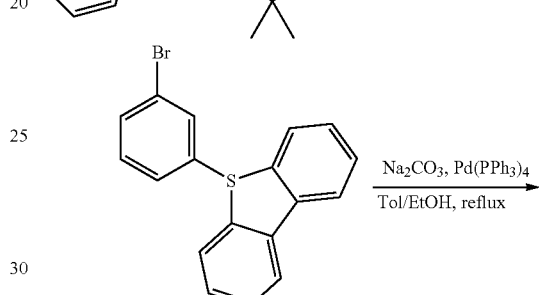

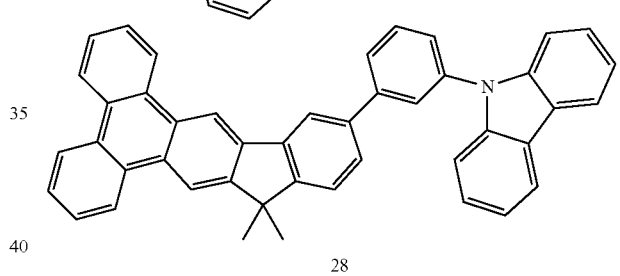

28

The synthesis of procedures are the same process with compound A12, the yield of the final product is 47%. MS (m/z, FAB+): 585.8. $^1$HNMR (CDCl$_3$, 400 MHz): chemical shift (ppm) 8.93 (s, 1H), 8.81 (d, J=8 Hz, 1H), 8.74 (d, J=8 Hz, 1H), 8.76~8.64 (m, 7H), 7.78~7.59 (m, 7H), 7.44~7.23 (m, 6H), 7.16~7.14 (m, 2H), 1.66 (s, 6H).

EXAMPLE 12

Synthesis of Compound A17

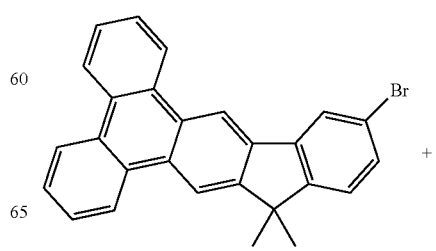

-continued

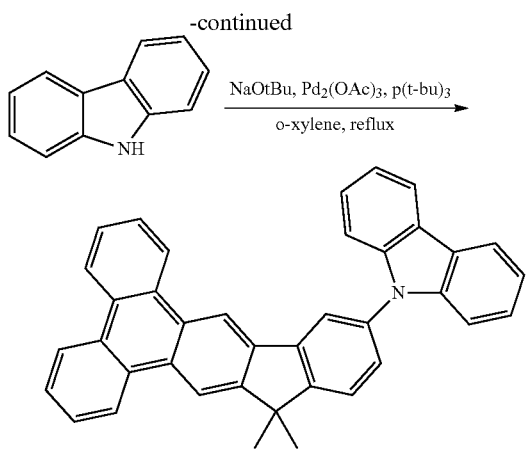

The synthesis of procedures are the same process with compound A13, the yield of the final product is 47%. MS (m/z, FAB+): 509.3. $^1$H NMR (CDCl$_3$, 400 MHz): chemical shift (ppm) 9.03 (s, 1H), 8.83 (d, J=8 Hz, 1H), 8.73 (d, J=8 Hz, 1H), 8.63~8.53 (m, 6H), 8.23~8.14 (m, 6H), 7.79~7.65 (m, 4H), 7.12~7.08 (m, 2H), 1.76 (s, 6H).

Synthesis of Intermediate Ie

Synthesis of 2-(biphenyl-2-yl)-7-bromo-9,9-dimethyl-9H-fluorene

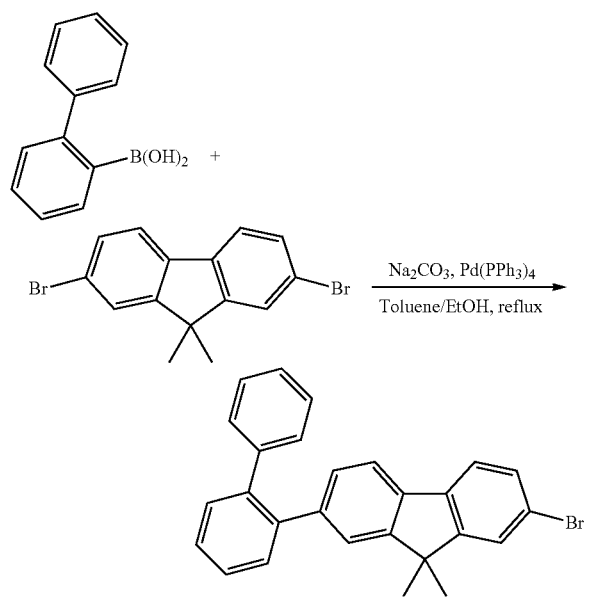

A mixture of 35.2 g (100 mmol) of 2,7-dibromo-9,9-dimethyl-9H-fluorene, 21.8 g (110 mmol) of biphenyl-2-ylboronic acid, 2.31 g (2 mmol) of Pd(PPh$_3$)$_4$, 75 ml of 2M Na2CO3, 150 ml of EtOH and 300 ml toluene was degassed and placed under nitrogen, and then heated at 100° C. for 12 h. After finishing the reaction, the mixture was allowed to cool to room temperature. The organic layer was extracted with ethyl acetate and water, dried with anhydrous magnesium sulfate, the solvent was removed and the residue was purified by column chromatography on silica to give product (26.8 g, 63.0 mmol, 63%) as a white solid.

Synthesis of 12-bromo-10,10-dimethyl-10H-indeno[2,1-b]triphenylene

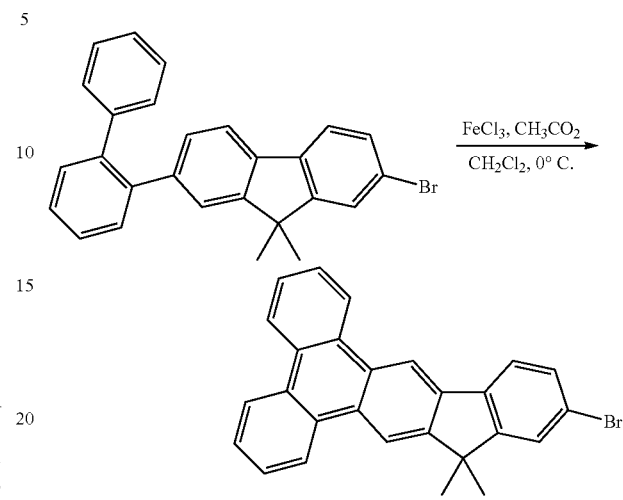

In a 3000 ml three-necked flask that had been degassed and filled with nitrogen, 26.8 g (60 mmol) of 2-(biphenyl-2-yl)-7-bromo-9,9-dimethyl-9H-fluorene was dissolved in anhydrous dichloromethane (1500 ml), 97.5 g (600 mmol) Iron(III) chloride was then added, and the mixture was stirred one hour. Methanol 500 ml were added to the mixture and the organic layer was separated and the solvent removed in vacuo. The residue was purified by column chromatography on silica (hexane-dichloromethane) afforded a white solid (10.7 g, 25.3 mmol, 40%). $^1$H NMR (CDCl$_3$, 400 MHz): chemical shift (ppm) 8.95 (s, 1H), 8.79~8.74 (m, 2H), 8.69~8.68 (m, 3H), 7.84 (d, J=8.0 Hz, 1H), 7.72~7.65 (m, 5H), 7.57 (d, J=8.0 Hz, 1H), 1.66 (s, 6H).

Synthesis of Intermediate Ie

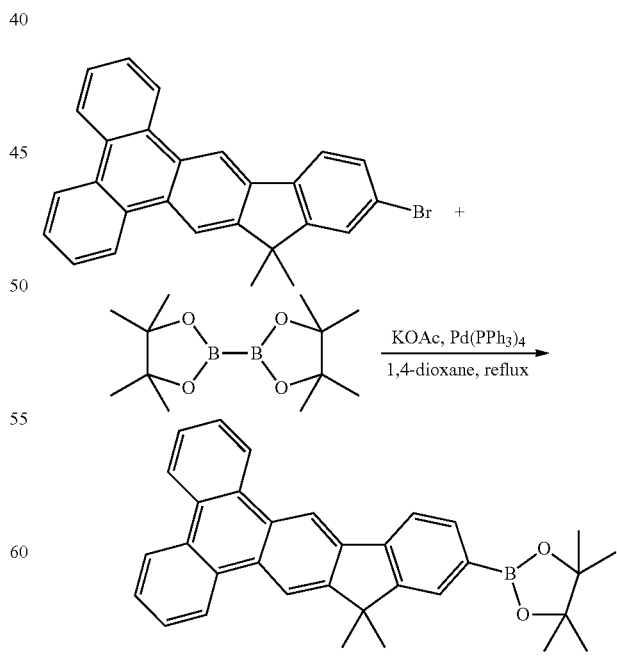

Intermediate Ie

A mixture of 10.7 g (25.3 mmol) of 12-bromo-10,10-dimethyl-10H-indeno-[1,2-b]triphenylene, 7.7 g (30.3 mmol) of bis(pinacolato)diboron, 0.3 g (0.26 mmol) of Pd(PPh$_3$)$_4$, 7.4 g (75.4 mmol) of potassium acetate, and 300 ml 1,4-dioxane was degassed and placed under nitrogen, and then heated at 90° C. for 16 h. After finishing the reaction, the mixture was allowed to cool to room temperature. The organic phase separated and washed with ethyl acetate and water. After drying over magnesium sulfate, the solvent was removed in vacuo. The residue was purified by column chromatography on silica (hexane-dichloromethane) to give product (9.5 g, 20.2 mmol, 80%) as a light-yellow solid; $^1$H NMR (CDCl$_3$, 400 MHz): chemical shift (ppm) 9.03 (s, 1H), 8.81 (d, J=7.84 Hz, 1H), 8.77 (d, J=7.88 Hz, 1H), 8.70~8.67 (m, 3H), 8.02~7.93 (m, 3H), 7.71~7.67 (m, 4H), 1.69 (s, 6H), 1.42 (s, 12H)

EXAMPLE 13

Synthesis of Compound A21

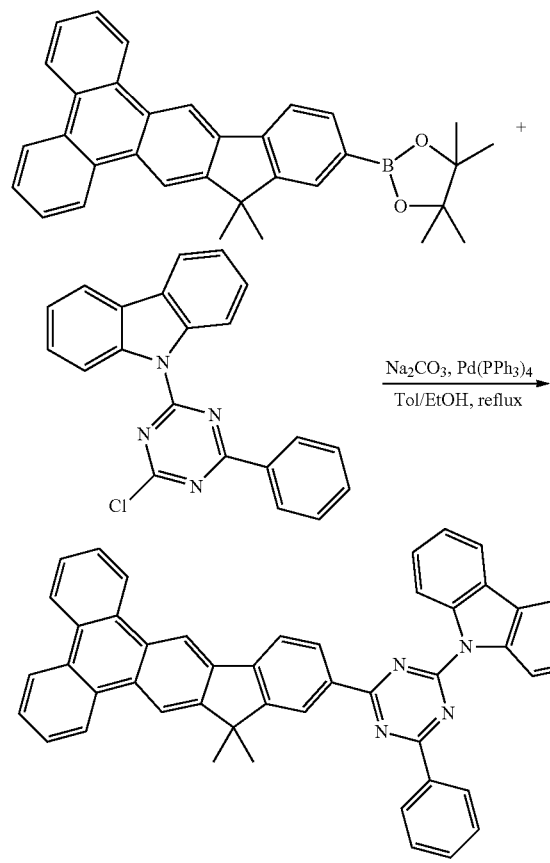

The synthesis of procedures are the same process with compound A23, the yield of the final product is 61%. MS (m/z, FAB+): 664.3. $^1$HNMR (CDCl$_3$, 400 MHz): chemical shift (ppm) 8.97 (s, 1H), 8.82 (d, J=8 Hz, 1H), 8.75 (d, J=8 Hz, 1H), 8.73~8.55 (m, 10H), 7.73~7.55 (m, 4H), 7.34~7.20 (m, 7H), 7.15~7.10 (m, 2H), 1.65 (s, 6H).

EXAMPLE 14

Synthesis of Compound A32

Synthesis of 3-(3-bromo-5-methylphenyl)-9-phenyl-9H-carbazole

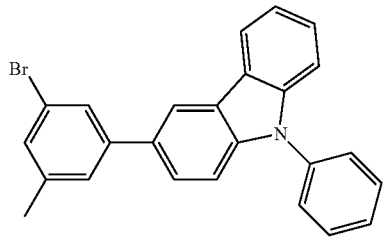 [SMILES: Cc1cc(Br)cc(-c2ccc3c(c2)c2ccccc2n3-c2ccccc2)c1]

Under N$_2$ condition, A mixture of 3-(N-phenylcarbazole) boronic acid (20 mmol, 5.74 g), 3-bromo-5-methyl-iodo-benzene (24 mmol, 7.13 g), 2M Na$_2$CO$_{3(aq)}$ (20 ml, 40 mmol), ethanol (40 ml) and toluene (40 ml), Pd(PPh$_3$)$_4$ (1.16 g, 1 mmol) was added and refluxed for 16 hours. After completion of the reaction, the mixture was extracted with ethyl acetate in a separating funnel, dried over anhydrous magnesium sulfate, filtered and concentrated. The concentrate was purified by silica gel column chromatography to give 5 g of product. Yield 61%.

Synthesis of Compound A32

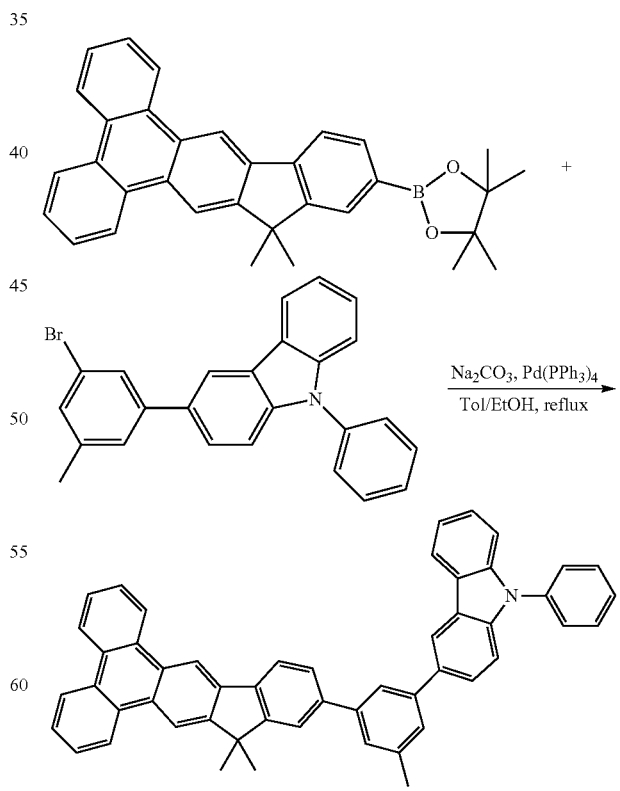

The synthesis of procedures are the same process with compound A12, the yield of the final product is 45%. MS (m/z, FAB+): 675.4. ¹HNMR (CDCl₃, 400 MHz): chemical shift (ppm) 8.96 (s, 1H), 8.82 (d, J=8 Hz, 1H), 8.75 (d, J=8 Hz, 1H), 8.73~8.61 (m, 8H), 8.23~8.15 (m, 4H), 7.73~7.55 (m, 6H), 7.34~7.20 (m, 5H), 7.15~7.10 (m, 2H), 2.24 (s, 3H), 1.65 (s, 6H).

Synthesis of Intermediate If

Synthesis of methyl 5-phenylpyrimidine-4-carboxylate

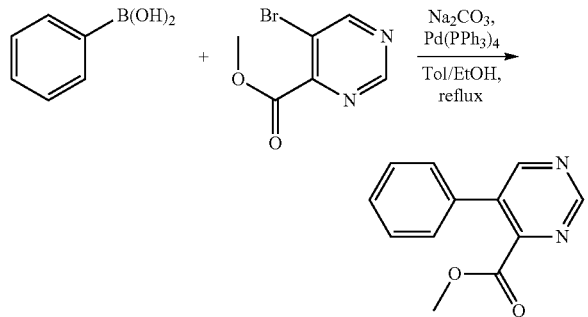

A mixture of methyl 5-bromopyrimidine-4-carboxylate (13 g, 60 mmol), phenylboronic acid (7.3 g, 60 mmol), 2M Na₂CO₃₍aq₎ (120 ml, 240 mmol), and Pd(PPh₃)₄ (1.8 g, 1.2 mmol) was dissolved in 400 ml toluene/130 ml ethanol under N₂. After stirring for 24 h at 80° C., the mixture was allowed to cool to room temperature. The residue was extract using dichloromethane/water, and organic layer was evaporated to dryness. The residue was purified by column chromatography on silica gel to obtained 5.9 g of methyl 5-phenylpyrimidine-4-carboxylate. Yield 45.4%.

Synthesis of 9,9-dimethyl-9H-indeno[2,1-d]pyrimidine

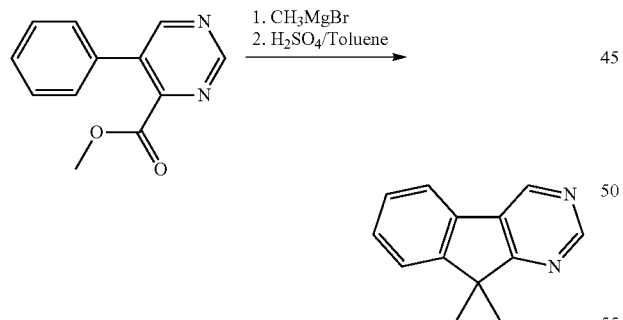

Methyl 5-phenylpyrimidine-4-carboxylate (8.6 g, 40 mmol) is dissolved in dry THF (160 ml), followed by adding 30 ml of CH₃MgBr (3M in ether). The reaction is reflux for overnight then stopped. After extraction with ethyl acetate, drying with anhydrous magnesium sulfate, rotary evaporation to remove solvent, intermediate product is obtained. The intermediate product is then dissolved in mixed solution of acetic acid (100 mL) and sulfuric acid (5 ml). The refluxing reaction is held for 4 hours then stopped and cooled. After extraction with ethyl acetate, drying with anhydrous magnesium sulfate, rotary evaporation to remove solvent, the residue was purified by column chromatography on silica gel to obtain 2.5 g of 9,9-dimethyl-9H-indeno[2, 1-d]pyrimidine. Yield 32%.

Synthesis of 7-bromo-9,9-dimethyl-9H-indeno[2,1-d]pyrimidine

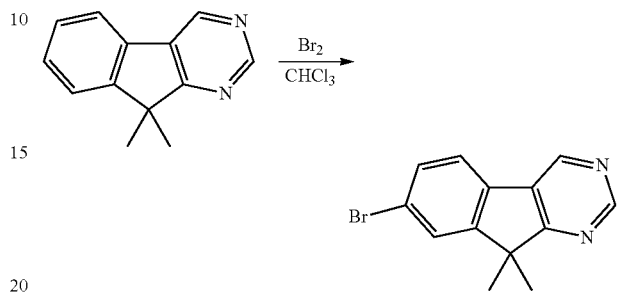

9,9-dimethyl-9H-indeno[2,1-d]pyrimidine (5.9 g, 30 mmol) was dissolved in chloroform (300 ml), protected from light and bromine (4.8 g, 30 mmol) diluted in chloroform (10 ml) was added drop wise. The mixture was stirred for 24 hours at room temperature, after which water (600 ml) was added, then the precipitated product was filtered off with suction, washed with MeOH and recrystallized from chloroform to give the 7-bromo-9,9-dimethyl-9H-indeno[2,1-d] pyrimidine 5.4 g. Yield 66%

Synthesis of 7-(biphenyl-2-yl)-9,9-dimethyl-9H-indeno[2,1-d]pyrimidine

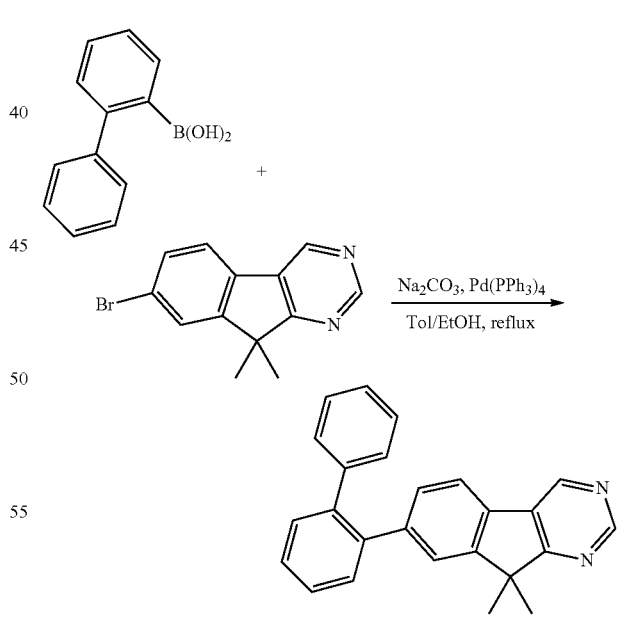

A mixture of 7-bromo-9,9-dimethyl-9H-indeno[2,1-d]pyrimidine (5 g, 18.3 mmol), biphenyl-2-ylboronic acid (3.6 g, 18.3 mmol), Pd(PPh₃)₄ (0.22 g, 0.184 mmol), 2M Na₂CO₃ (19 ml), 30 ml of EtOH and 100 ml toluene was degassed and placed under nitrogen, and then heated at 90° C. for 24 h. After finishing the reaction, the reaction mixture was cool to room temperature. The organic layer was extracted with ethyl acetate and water, dried with anhydrous magnesium sulfate, the solvent was removed and the residue was purified by column chromatography on silica gel to obtain 7-(biphenyl-2-yl)-9,9-dimethyl-9H-indeno[2,1-d]pyrimidine 3.5 g. Yield 56%.

Synthesis of Intermediate If

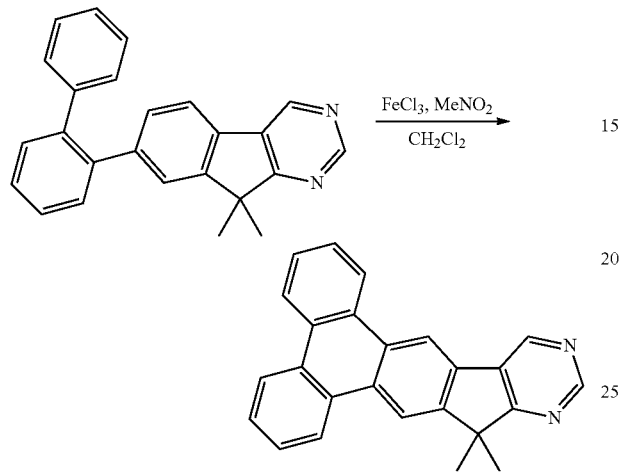

Under nitrogen condition, 7-(biphenyl-2-yl)-5,5-dimethyl-5H-indeno[1,2-b]-pyridine (3.48 g, 10 mmol) was dissolved in anhydrous dichloromethane (250 ml), 1.62 g (100 mmol) Iron(III) chloride was then added, and the mixture was stirred one hour. Methanol 10 ml were added to the mixture and the organic layer was separated and the solvent removed in vacuum. The residue was purified by column chromatography on silica gel to obtain 1.35 g of the product. Yield 39%.

Synthesis of Intermediate Ig

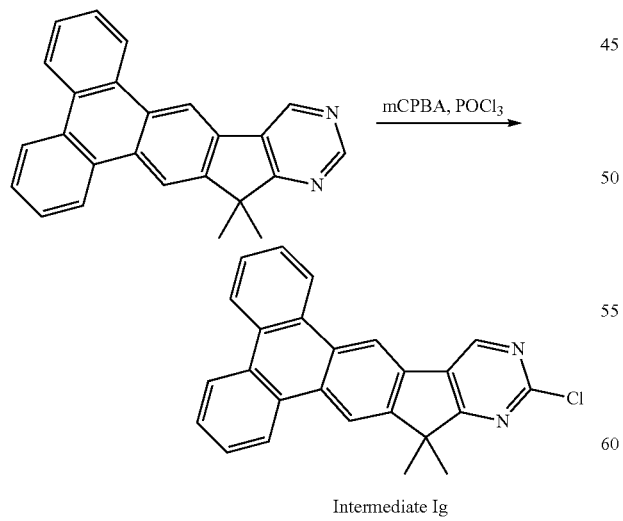

Intermediate Ig 5.0 g (14.4 mmol) of intermediate If was dissolved in 100 ml of chloroform, 3.2 g (18.7 mmol) of mCPBA was added to the solution at 25° C. with stirring, and stirred at room temperature for 2 hours. After the reaction, sodium thiosulfate was added to the mixture, and dried over sodium sulfate and filtrated. The filtrate was concentrated and the slurry was washed with chloroform, the crude material was purified by chromatography on silica gel to obtain 3.9 g of an N-oxide of intermediate. Yield 74.5%.

Subsequently, 20 ml of phosphorus oxychloride was added to 3.9 g (10.7 mmol) of the above N-oxide, and heated and stirred at 95° C. for 10 hours. The reaction was concentrated, and then chloroform (200 ml) was added to the concentrate. The chloroform solution was added dropwise to a saturated aqueous solution of sodium hydrogen carbonate, and stirred for 1 hour. The mixture was extracted with chloroform, washed with sat. $NaCl_{(aq)}$, dried over sodium sulfate, and concentrated, the crude material was purified by chromatography on silica gel to give 1.8 g. Yield 43.9%, $^1$H NMR (CDCl$_3$, 400 MHz): chemical shift (ppm) 8.99 (s, 1H), 8.90 (d, J=8.0 Hz, 1H), 8.79~8.72 (m, 4H), 7.80 (m, 1H), 7.72~7.60 (m, 4H), 1.65 (s, 6H).

EXAMPLE 15

Synthesis of Compound A16

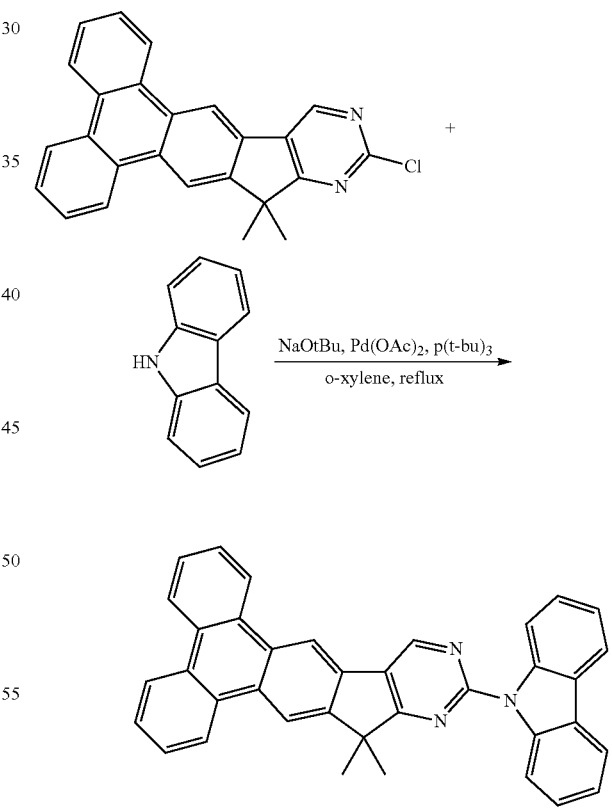

The synthesis of procedures are the same process with compound A13, the yield of the final product is 61%. MS (m/z, FAB+): 511.6. $^1$H NMR (CDCl$_3$, 400 MHz): chemical shift (ppm) 9.12 (s, 1H), 9.05 (s, 1H), 8.91 (d, J=8 Hz, 1H), 8.82 (d, J=8 Hz, 1H), 8.73~8.66 (m, 5H), 8.13~7.98 (m, 4H), 7.68~7.59 (m, 4H), 7.20~7.17 (m, 2H), 1.66 (s, 6H).

EXAMPLE 16

Synthesis of Compound A28

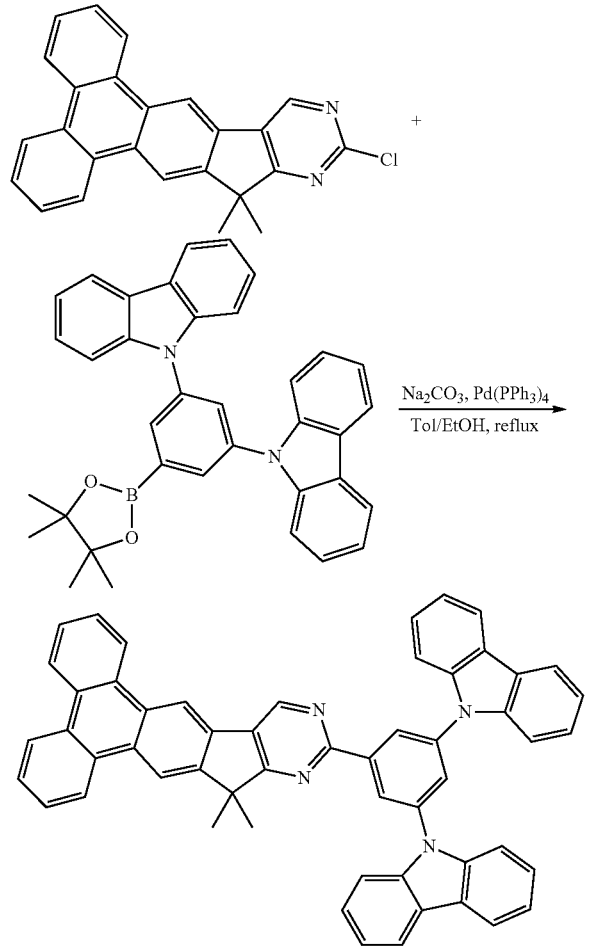

The synthesis of procedures are the same process with compound A1, the yield of the final product is 36%. MS (m/z, FAB+): 752.3. $^1$H NMR (CDCl$_3$, 400 MHz): chemical shift (ppm) 9.08 (s, 1H), 8.90 (m, 2H), 8.82 (d, J=8 Hz, 1H), 8.74~8.62 (m, 8H), 8.23~8.14 (m, 8H), 7.69~7.48 (m, 4H), 7.34~7.28 (m, 4H), 7.20~7.14 (m, 2H), 1.66 (s, 6H).

EXAMPLE 17

Synthesis of Compound A38

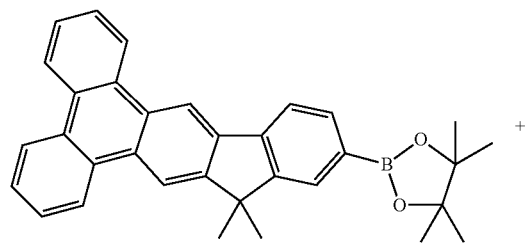

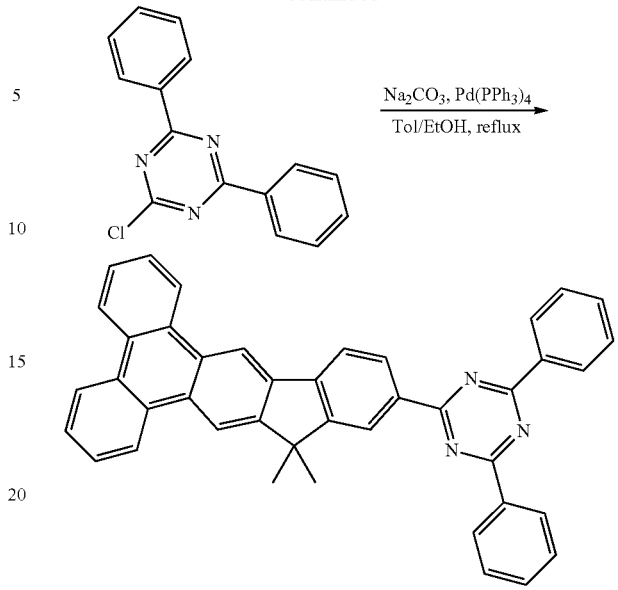

The synthesis of procedures are the same process with compound A23, the yield of the final product is 67%. MS (m/z, FAB+): 575.3 $^1$HNMR (CDCl$_3$, 400 MHz): chemical shift (ppm) 9.04 (s, 1H), 8.88~8.86 (m, 2H), 8.82~8.79 (m, 5H), 8.76 (d, J=8 Hz, 1H), 8.72 (s, 1H), 8.67~8.65 (m, 2H), 8.11 (d, J=8 Hz, 1H), 7.73~7.58 (m, 10H), 1.79 (m, 6H).

General Method of Producing Organic EL Device

ITO-coated glasses with 9~12 ohm/square in resistance and 120~160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit (10$^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material. This is achieved by co-vaporization from two or more sources.

Dipyrazino[2,3-f:2,3-]quinoxaline-2,3,6,7,10,11-hexacarbonitrile (HAT-CN) is used as hole injection layer in this organic EL device. N,N-Bis(naphthalene-1-yl)-N,N-bis(phenyl)-benzidine (NPB) is most widely used as the hole transporting layer. 10,10-Dimethyl-12-(4-(pyren-1-yl)phenyl)-10H-indeno[1,2-b]triphenylene (PT-312, US20140175384) are used as blue emitting host and N1,N1,N6,N6-tetram-tolylpyrene-1,6-diamine (D1) is used as blue guest. 4,7-Diphenyl-2,9-bis(4-(1-phenyl-1H-benzo[d]imidazole-2-yl)phenyl)-1,10-phenanthroline (LT-N8001,U.S. Pat. No. 7,754,348) is used as electron transporting material (ETM) to co-deposit with 5% Li or co-deposit with 8-hydroxyquinolato-lithium (LiQ) in organic EL device. Bis(2-methyl-8-quinolinolate)-4-(phenylphenolato)aluminium (BAlq) is used as hole blocking material (HBM) and phosphorescent host for phosphorescent system, Bis(2-phenylpyridinato)(2,4-diphenylpyridinato)iridium(III) (D1) are used as phosphorescent dopant. The prior art of OLED materials for producing standard organic EL device control and comparable material in this invention shown its chemical structure as following:
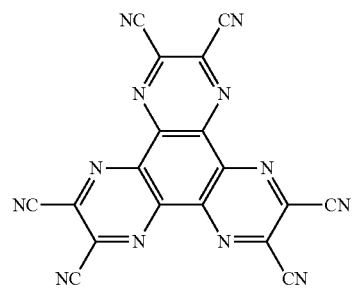
HAT-CN
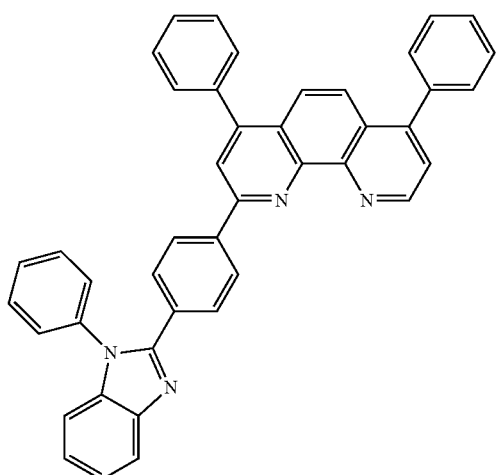
LT-N8001
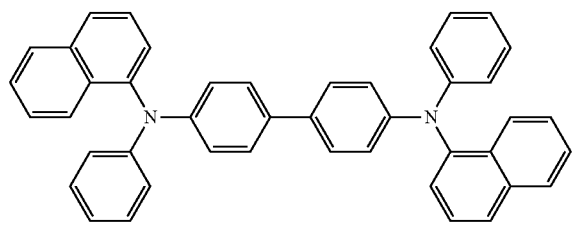
NPB
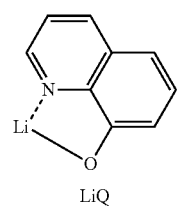
LiQ
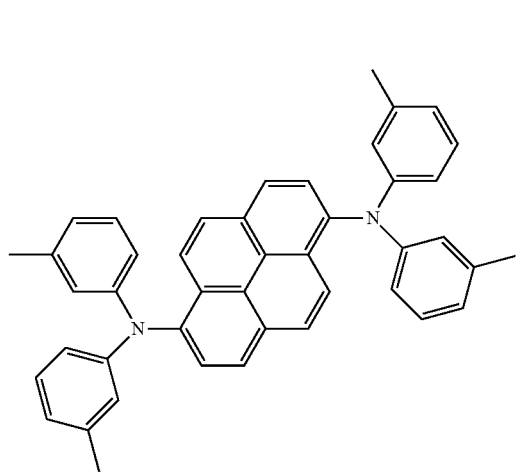
D1
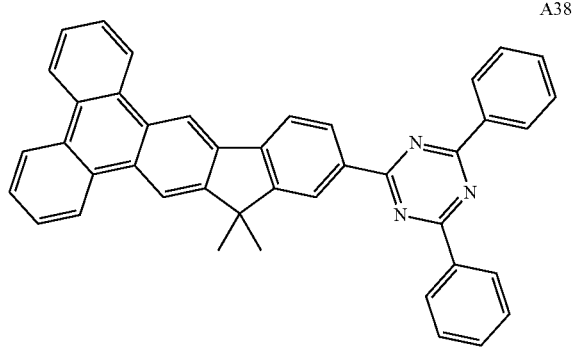
A38
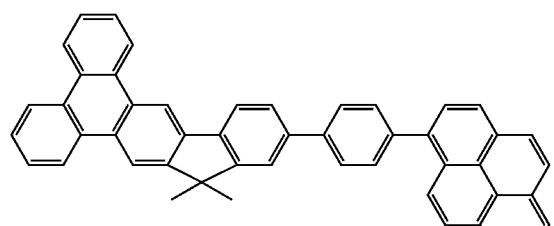
PT-312
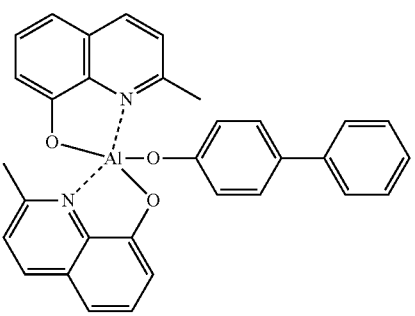
BAlq

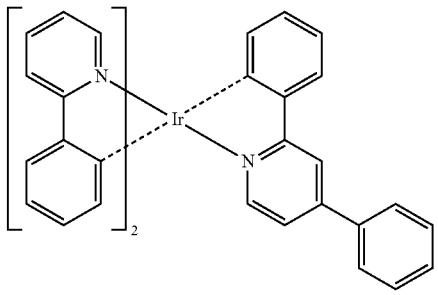

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ, MgO, or $Li_2O$. On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

EXAMPLE 18

Using a procedure analogous to the above mentioned general method, fluorescent blue-emitting organic EL device having the following device structure were produced (See The FIGURE): ITO/HAT-CN(20 nm)/NPB(130 nm)/PT-312 doped 5% D1 (30 nm)/HBM(10 nm)/ETM co-deposit LiQ (ETM:LiQ, ratio=1:1 (40 nm)/LiQ(1 nm)/Al (160 nm). The I-V-B (at 1000 nits) and half-life time of fluorescent blue-emitting organic EL device testing report as Table 1, The half-life time is defined that the initial luminance of 1000 cd/m² has dropped to half.

TABLE 1

| HBM | ETM | Voltage (V) | Efficiency (lm/w) | CIE(y) | Half-lifetime (hour) |
|---|---|---|---|---|---|
| — | LT-N8001 | 5.6 | 2.8 | 0.183 | 140 |
| BAlq | LT-N8001 | 5.8 | 3.1 | 0.184 | 220 |

TABLE 1-continued

| HBM | ETM | Voltage (V) | Efficiency (lm/w) | CIE(y) | Half-lifetime (hour) |
|---|---|---|---|---|---|
| — | A15 | 4.8 | 2.6 | 0.189 | 200 |
| — | A21 | 5.3 | 3.3 | 0.187 | 180 |
| — | A25 | 5.1 | 3.2 | 0.177 | 280 |
| — | A31 | 4.5 | 3.7 | 0.180 | 300 |
| BAlq | A31 | 4.8 | 4.0 | 0.178 | 250 |
| — | A38 | 4.0 | 4.7 | 0.189 | 290 |
| BAlq | A38 | 4.2 | 4.9 | 0.189 | 330 |

EXAMPLE 19

Using a procedure analogous to the above mentioned general method, phosphorescent emitting organic EL device having the following device structures are produced (See The FIGURE): ITO/HAT-CN(20 nm)/NPB(130 nm)/phosphorescent host(PHhost)+15% D2 (30 nm)/HBM(15 nm)/A38 co-deposit LiQ(A38:LiQ, ratio=1:1)(40 nm)/LiQ(1 nm)/Al (160 nm). The I-V-B (at 1000 nits) and half-life time of phosphorescent emitting organic EL device testing report as Table 2. The half-life time is defined that the initial luminance of 3000 cd/m² has dropped to half.

TABLE 2

| PHhost(H1 + H2) H1:H2 = 1:1 | HBM | Voltage (V) | Efficiency (lm/w) | CIE(x, y) | Half-life time (hour) |
|---|---|---|---|---|---|
| BAlq | BAlq | 6.8 | 12 | 0.45, 0.58 | 350 |
| A2 + A27 | BAlq | 5.3 | 26 | 0.43, 0.58 | 400 |
| A2 + A27 | A27 | 3.8 | 37 | 0.42, 0.56 | 650 |
| A12 + A27 | A27 | 4.1 | 21 | 0.42, 0.56 | 350 |
| A17 + A28 | A27 | 4.2 | 18 | 0.42, 0.56 | 400 |
| A31 + A28 | A27 | 3.7 | 22 | 0.42, 0.56 | 380 |
| A33 + A27 | A27 | 3.9 | 18 | 0.42, 0.56 | 200 |
| A34 + A28 | A27 | 4.2 | 24 | 0.42, 0.57 | 110 |
| A2 + A23 | A27 | 3.4 | 30 | 0.42, 0.57 | 560 |
| A2 + A28 | A27 | 3.5 | 38 | 0.41, 0.56 | 800 |
| A2 + A21 | A27 | 3.9 | 29 | 0.41, 0.56 | 750 |
| A2 + A33 | A27 | 3.7 | 16 | 0.42, 0.56 | 180 |
| A2 + A23 | A28 | 3.3 | 31 | 0.43, 0.57 | 600 |
| A2 + A28 | A28 | 3.2 | 36 | 0.43, 0.57 | 750 |
| A2 + A21 | A28 | 3.0 | 32 | 0.42, 0.56 | 650 |
| A2 + A30 | A28 | 3.8 | 29 | 0.43, 0.56 | 250 |
| A2 + A31 | A28 | 3.4 | 14 | 0.42, 0.56 | 200 |

In the above preferred embodiments for organic EL device test report (see Table 1 and Table 2), we show that the organic material formula (A) in the present invention used as hole blocking material, electron transport material or phosphorescent host display good performance than the prior art of organic EL materials.

To sum up, the present invention discloses a novel organic material which can be used for organic EL device is disclosed. The mentioned organic material are represented by the following formula (A):

formula(A)

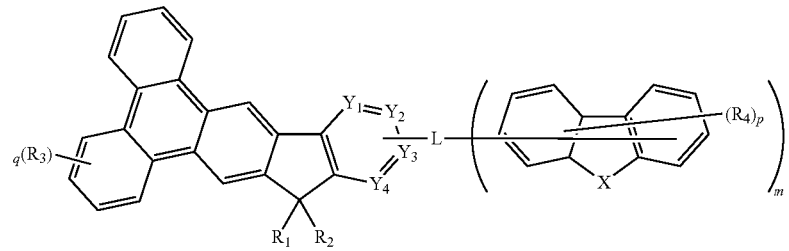

Wherein m represent 0 to 2, and when m represent 1 or 2, L represent a single bond, a substituted or unsubstituted arylene group having 6 to 40 ring carbon atoms, or a substituted or unsubstituted heterarylene group having 3 to 40 ring carbon atoms. When m represent 0, L represent a substituted or unsubstituted heterarylene group having 3 to 40 ring carbon atoms. X represent O, S, $NR_5$. $Y_1$ to $Y_4$ each independently represent nitrogen atom or $CR_6$. $R_5$ and $R_6$ independently represent a hydrogen atom, a substituent, or a bond to L. p represent an integer of 0 to 7, q represent an integer of 0 to 10. $R_1$ to $R_4$ independently selected from the group consisting of a hydrogen atom, a halide, alkyl group having 1 to 20 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 3 to 30 carbon atoms.

The invention claimed is:

1. An organic material with a general formula (A) as following:

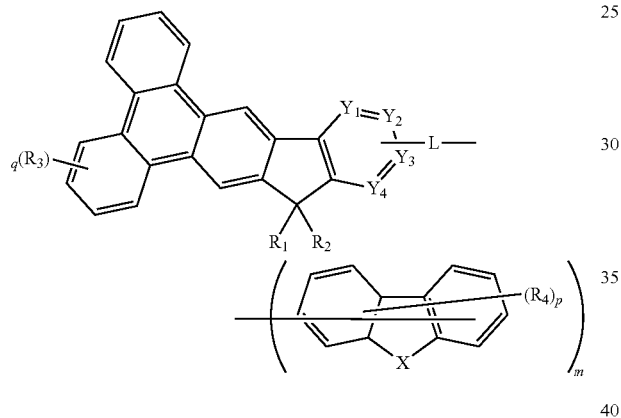

Wherein m represents 0 to 2, and when m represents 1 or 2, L represents a single bond, a substituted or unsubstituted arylene group having 6 to 40 ring carbon atoms, or a substituted or unsubstituted heterarylene group having 3 to 40 ring carbon atoms; when m represents 0, L represents a substituted or unsubstituted heterarylene group having 3 to 40 ring carbon atoms; X represents O, S, $NR_5$; at least one of positions from $Y_1$ to $Y_4$ represents nitrogen atom, and rest of the positions from $Y_1$ to $Y_4$ represent nitrogen atom or $CR_6$; $R_5$ and $R_6$ independently represents a hydrogen atom, a substituent, or a bond to L; p represents an integer of 0 to 7, q represents an integer of 0 to 10; $R_1$ to $R_4$ are independently selected from the group consisting of a hydrogen atom, a halide, an alkyl group having 1 to 20 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 3 to 30 carbon atoms.

2. The organic material with a general formula (A) according to claim 1, wherein when the L is not represented by a single bond, the m represents 1 or 2, the L is consisted of a group representing as following:

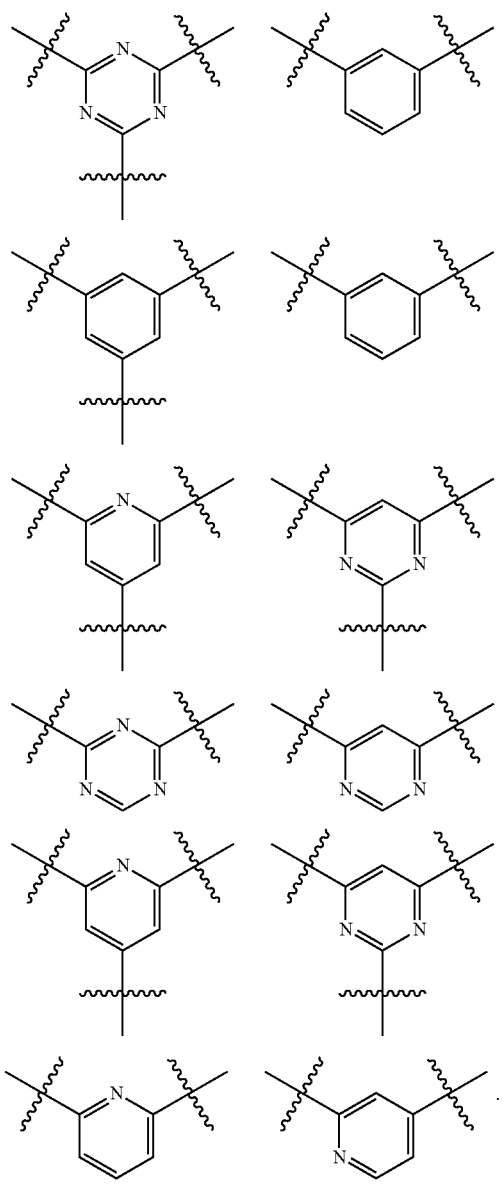

3. The organic material with a general formula (A) according to claim 1, wherein when the m represents 0, the L represents a substituted or unsubstituted heterarylene group consisting of a group representing as following:

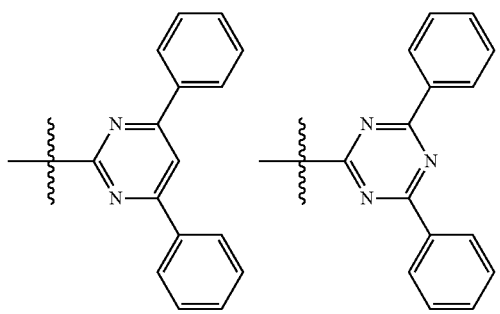

-continued

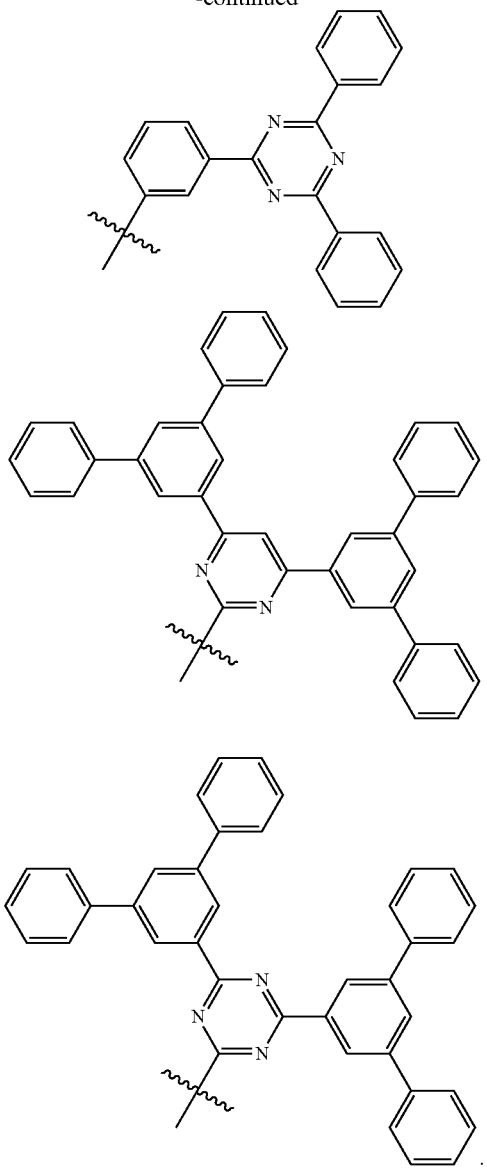

4. An organic electroluminescent device comprising a pair of electrodes consisting of a cathode and an anode and between the pairs of electrodes comprising at least a layer of the organic material with a general formula (A), the general formula (A) is shown as the following:

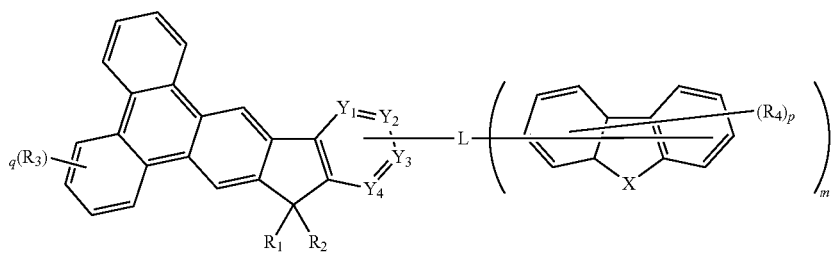

Wherein m represents 0 to 2, and when m represents 1 or 2, L represents a single bond, a substituted or unsubstituted arylene group having 6 to 40 ring carbon atoms, or a substituted or unsubstituted heterarylene group having 3 to 40 ring carbon atoms; when m represents 0, L represents a substituted or unsubstituted heterarylene group having 3 to 40 ring carbon atoms; X represents O, S, NR$_5$; at least one of positions from Y$_1$ to Y$_4$ represents nitrogen atom, and rest of the positions from Y$_1$ to Y$_4$ represent nitrogen atom or CR$_6$; R$_5$ and R$_6$ independently represents a hydrogen atom, a substituent, or a bond to L; p represents an integer of 0 to 7, q represents an integer of 0 to 10; R$_1$ to R$_4$ are independently selected from the group consisting of a hydrogen atom, a halide, an alkyl group having 1 to 20 carbon atoms, a substituted or unsubstituted aryl group having 6 to 30 carbon atoms, a substituted or unsubstituted aralkyl group having 6 to 30 carbon atoms, a substituted or unsubstituted heteroaryl group having 3 to 30 carbon atoms, wherein the at least a layer of the organic material includes an electron transport layer selected from a group consisting of Li, Ca, and 8-hydroxyquinolinolato-lithium.

5. The organic electroluminescent device according to claim 4, wherein the at least a layer of the organic material includes an emitting layer, the emitting layer comprises the organic material with the general formula (A).

6. The organic electroluminescent device according to claim 5, wherein the emitting layer comprising the organic material with the general formula (A) is a phosphorescent host material or thermally activated delayed fluorescence host material.

7. The organic electroluminescent device according to claim 5, wherein the emitting layer comprises a phosphorescent dopant or thermally activated delayed fluorescence dopant.

8. The organic electroluminescent device according to claim 7, wherein the phosphorescent dopant is iridium (Ir) complex.

9. The organic electroluminescent device according to claim 4, wherein the at least a layer of the organic material includes a hole blocking electron transport layer, the hole blocking electron transport layer comprises the general formula (A).

10. The organic material with a general formula (A) according to claim 1, wherein the organic material with the general formula (A) is selected from the group consisting of A1, A5, A10, A11, A13, A14, A15, A16, A25, A28, A30, A33, A35, A36, A37 and A39:

A1
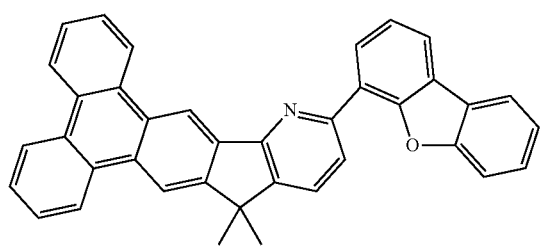
A14
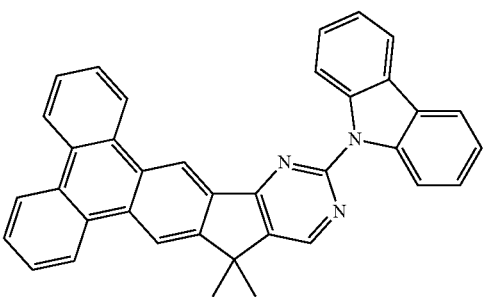
A5
A15
A10
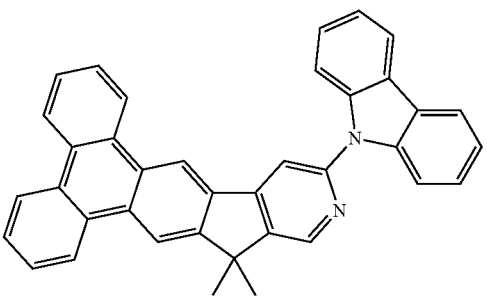
A11
A16
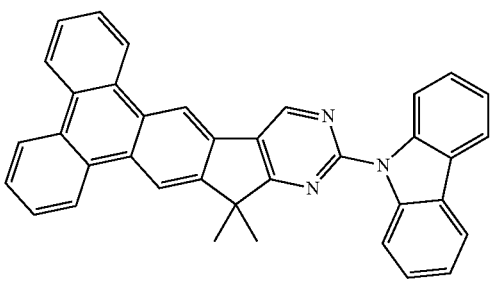
A13
A25
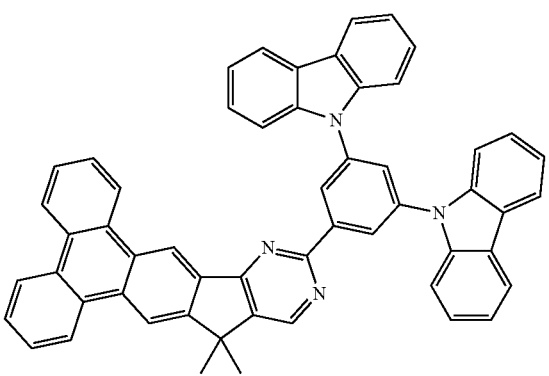

A28
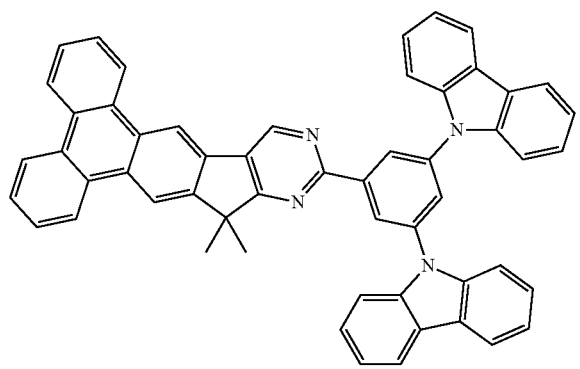
A35
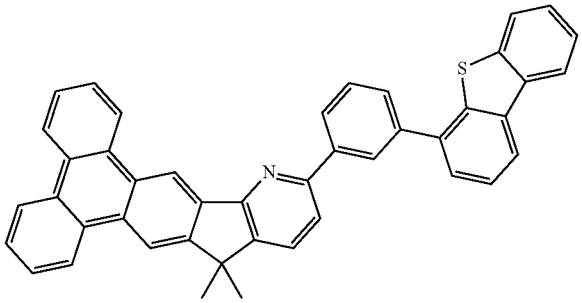
A30
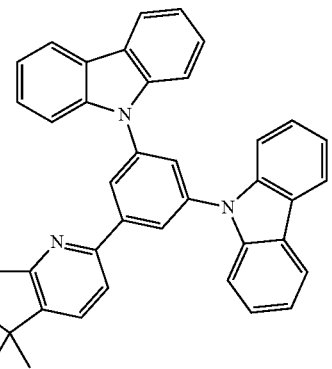
A36
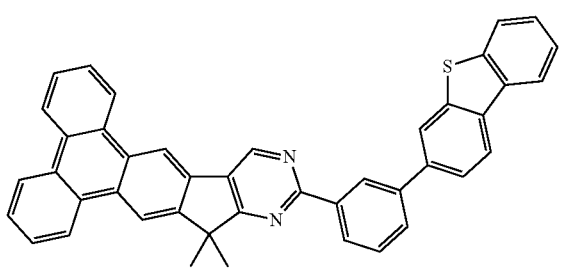
A37
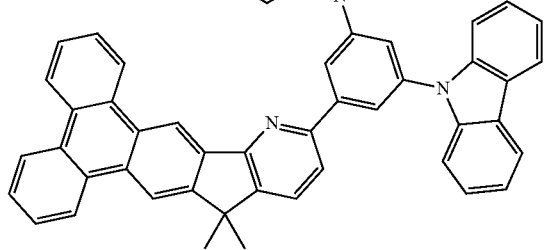
A33
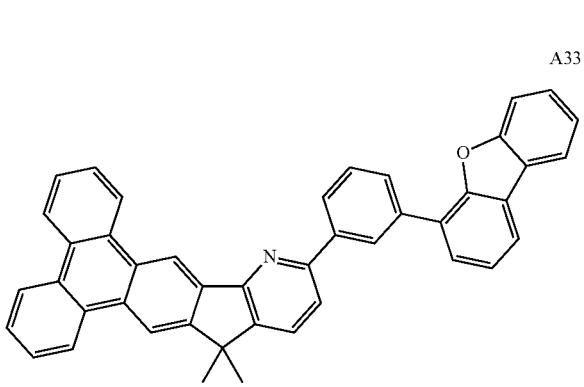
A39
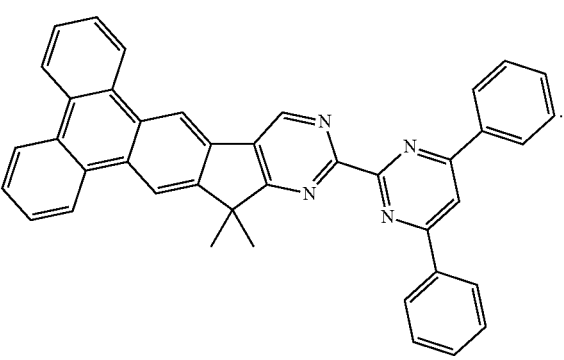
* * * * *